(12) United States Patent
Chow et al.

(10) Patent No.: US 7,048,932 B2
(45) Date of Patent: May 23, 2006

(54) PREPARATION AND STANDARDIZATION OF IMMUNOMODULATORY PEPTIDE-LINKED GLUCANS WITH VERIFIABLE ORAL ABSORBABILITY FROM CORIOLUS VERSICOLOR

(75) Inventors: Albert H. L. Chow, Ma On Shan (HK); Kevin K. W. Chu, Kowloon (HK)

(73) Assignee: The Chinese University of Hong Kong, Shatin (HK)

( * ) Notice: Subject to any disclaimer, the term of this patent is extended or adjusted under 35 U.S.C. 154(b) by 212 days.

(21) Appl. No.: 10/236,996

(22) Filed: Sep. 6, 2002

(65) Prior Publication Data

US 2003/0224014 A1    Dec. 4, 2003

Related U.S. Application Data

(60) Provisional application No. 60/383,339, filed on May 22, 2002.

(51) Int. Cl.
*A61K 35/78*    (2006.01)

(52) U.S. Cl. .................................. 424/195.15; 424/725

(58) Field of Classification Search ............ 424/195.15
See application file for complete search history.

(56) References Cited

U.S. PATENT DOCUMENTS

| | | | |
|---|---|---|---|
| 4,051,314 A | 9/1977 | Ohtsuka et al. | |
| 4,140,578 A | 2/1979 | Yoshikumi et al. | |
| 4,159,225 A | 6/1979 | Yoshikumi et al. | |
| 4,202,885 A | 5/1980 | Asano et al. | |
| 4,202,969 A | 5/1980 | Ueno et al. | |
| 4,225,673 A | 9/1980 | Sugiura et al. | |
| 4,228,275 A | 10/1980 | Asano et al. | |
| 4,229,570 A | 10/1980 | Ueno et al. | |
| 4,237,266 A | 12/1980 | Sugiura et al. | |
| 4,268,505 A | 5/1981 | Yoshikumi et al. | |
| 4,271,151 A * | 6/1981 | Hotta et al. ..................... 514/8 |
| 4,289,688 A | 9/1981 | Hotta et al. | |
| 4,614,733 A | 9/1986 | Yoshikumi et al. | |
| 4,663,438 A | 5/1987 | Yoshikumi et al. | |
| 4,818,752 A | 4/1989 | Williams et al. | |
| 4,820,689 A | 4/1989 | Ikuzawa et al. | |
| 4,851,395 A | 7/1989 | Ueno et al. | |
| 4,975,421 A | 12/1990 | Williams et al. | |
| 4,975,422 A | 12/1990 | Kanoh et al. | |
| 5,008,243 A | 4/1991 | Ikuzawa et al. | |
| 5,374,714 A | 12/1994 | Yang et al. | |
| 5,693,610 A * | 12/1997 | Matsunaga et al. ............ 514/8 |
| 5,756,318 A | 5/1998 | Kosuna | |
| 5,824,648 A | 10/1998 | Yang et al. | |
| 6,087,335 A | 7/2000 | Yang et al. | |

OTHER PUBLICATIONS

Sugiura, M. et al,; "Studies on Antitumor Polysaccharides, Especially D-II, From Mycelium of Coriolus Versicolor," Japan. J. Pharmacol. 30, 503-513 (1980).*
http://www.wholefoods.com/healthinfo/mannitol.html; website.*
NG, T.B., "Review of the Research on the Protein-Bound Polysaccharide (Polysaccharopeptide, PSP) from the Mushroom *Coriolus versicolor* (Basidiomycetes: Polyporacae)," *Gen. Pharmac.*, 1998, 30(1):1-4.
Tsukagoshi, S, et al., "Krestin (PSK)," *Cancer Treatment Reviews*, 1984, 11:131-155.
Li, X.Y., "Advances in Immunomodulating Studies of PSP," 1999 pp. 39-46, in *Advanced Research in PSP*, Yang, Q., Ed., Hong Kong Association for Health Care Ltd., Hong Kong.

* cited by examiner

*Primary Examiner*—Susan Coe
*Assistant Examiner*—S. B. McCormick-Ewoldt
(74) *Attorney, Agent, or Firm*—Townsend and Townsend and Crew LLP

(57) ABSTRACT

This invention provides compositions and methods for stimulating the immune system. Such methods include administering an extract, purified peptide-linked glucan or active component thereof from *Coriolus versicolor*. The methods are particularly useful for prophylactic and therapeutic treatment of secondary immunodeficiency, wherein the immunodeficiency is the result of an infection, a malignant neoplastic disease, an autoimmune disease, a protein losing state, an immunosuppressive treatment, surgery or anesthesia.

10 Claims, 17 Drawing Sheets

SEQUENCE LISTING

<160> NUMBER OF SEQ ID NOS: 1

<210> SEQ ID NO 1
<211> LENGTH: 6
<212> TYPE: PRT
<213> ORGANISM: Coriolus versicolor

<400> SEQUENCE: 1

Asp Cys Pro Pro Cys Glu
 1               5

PREPARATION AND STANDARDIZATION OF IMMUNOMODULATORY PEPTIDE-LINKED GLUCANS WITH VERIFIABLE ORAL ABSORBABILITY FROM CORIOLUS VERSICOLOR

CROSS-REFERENCES TO RELATED APPLICATIONS

This application is a nonprovisional of U.S. Application No. 60/383,339 filed May 22, 2002, which is incorporated herein by reference in its entirety.

STATEMENT AS TO RIGHTS TO INVENTIONS MADE UNDER FEDERALLY SPONSORED RESEARCH OR DEVELOPMENT

Not Applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The importance of individual components of immunologic function to the host's natural defense has been most clearly revealed when isolated deficiencies have led to clinical disease. Because such abnormalities can now be effectively detected and defined by new laboratory methods, diseases of immunodeficiency are being discovered with increasing frequency. Immunodeficiency disorders must be considered in two major categories: the primary immunodeficiency, often genetically determined, and secondary immunodeficiency states. The latter occur as complications of infections and infestations, gastrointestinal disorders, malnutrition, aging, lymphoid malignancies, other cancers and many other diseases. Immunodeficiency of varying severity is also encountered as a side effect of many treatment modalities, including radiation therapy and chemotherapy for cancer. From this perspective, the primary and secondary immunodeficiencies are not rare diseases. These problems have necessitated a search for novel therapeutic agents that have the property of immunopotentiation.

The discovery of the involvement of the immune system in the pathogenesis of an ever-increasing number of diseases has inevitably led to attempts to modify the course of these diseases, by manipulating the various elements of the immunological machinery. Stimulation of the immune system is invariably the choice for the mitigation of the immunodeficient state. This approach, for which there are several sets of potent agents (i.e. bacillus Calmette-Guerin, endotoxins) available today, holds particular promise in two major therapeutic areas in medicine—cancer and infectious diseases.

According to the concept of immunosurveillance, the immune system eliminates malignant cells when they appear. The role of T cells, and more recently of macrophages, natural killer cells against cancer has been reported. In addition, even if the antitumor immune response is not principally involved in the control of tumor growth, it is likely that adequate immunostimulation could elicit an effective immune response or render effective an otherwise ineffective response. All these considerations have justified the use of immunostimulation in the treatment of cancer, as an auxiliary method to surgery, radiotherapy or chemotherapy[1].

Immunostimulants have also been extensively studied in infectious diseases in animal models. Infected subjects, who present a recognized immunodeficiency problem and often show infections with opportunistic microbes, should theoretically benefit from immunotherapy. It should be noted, however, that infections not obviously associated with immunodeficiency can also be treated with immunopotentiating agents, since enhancement of a immunological response may help to eliminate a particularly virulent agent which depresses normal physiological responses. Furthermore, particular attention should be given to the case of aging subjects, who often respond poorly to a number of vaccines (e.g. influenza).

BRIEF SUMMARY OF THE INVENTION

In one aspect, the invention provides a purified extract of *Coriolus versicolor* comprising at least one peptide-linked glucan comprising glucose molecules linked by a (1→3) linkage, having a molecular weight of 0.7 kDa to 5 kDa as determined by size exclusion chromatography; and immune stimulating activity. In another aspect, the invention provides an isolated peptide-linked glucan of *Coriolus versicolor* comprising a plurality of glucose molecules linked by a (1→3) linkage; a molecular weight of 0.7 kDa to 3.0 kDa as determined by size exclusion chromatography; and, the isolated peptide-linked glucan and an active component thereof have immune stimulating activity. The invention further provides pharmaceutical compositions comprising an isolated peptide-linked glucan of *Coriolus versicolor* and/or an active component thereof.

In another aspect, the invention provides methods of purifying a peptide-linked glucan from *Coriolus versicolor* comprising the steps of: treating *Coriolus versicolor* with alkali, and separating a supernatant; subjecting the supernatant to cationic exchange; subjecting eluate from the cationic exchange to anionic exchange; subjecting eluate from the anionic exchange to a size fractionation technique, and collecting a fraction comprising peptide-linked glucan having a molecular weight of 0.7 to 5 kDa.

In another aspect, the invention provides methods of stimulating an immune response, comprising contacting cells of the immune system with the extract, peptide-linked glucan or active component thereof. In another aspect, the invention provides a method of treating a patient in need of stimulation of the immune system, comprising administering to the patient an effective amount of an extract, purified peptide-linked glucan or active component thereof of claims to stimulate the immune response.

BRIEF DESCRIPTION OF THE DRAWINGS

FIG. 2A is a size exclusion chromatogram which shows the elution profile of the protein component of CV crude extract. FIG. 2B is a size exclusion chromatogram of CV crude extract which shows the elution profile of the carbohydrate component of CV crude extract.

FIG. 6A illustrates the in vivo effect on viable splenocytes of mice treated with CV crude extract administered i.p. (3 day dosing schedule). FIG. 6B illustrates the ex vivo proliferative effect on viable bone marrow cells of mice treated with CV crude extract administered i.p. (3 day dosing schedule).

FIG. 7A illustrates the in vivo effect on viable splenocytes of normal mice treated with CV crude extract administered orally (7 day dosing schedule). FIG. 7B illustrates the ex vivo proliferative effect on viable bone marrow cells of normal mice treated with CV crude extract administered orally (7 day dosing schedule).

FIG. 8A illustrates the in vivo effect on viable splenocytes and on viable bone marrow cells of immunocompromised mice treated with CV crude extract administered i.p. (3 day dosing schedule). FIG. 8B illustrates the in vivo effect on viable splenocytes and on viable bone marrow cells of immunocompromised mice treated with CV crude extract administered orally (seven day dosing schedule). FIG. 8C illustrates the in vivo effect on viable splenocytes and on viable bone marrow cells of severely immunocompromised mice treated with CV crude extract administered orally (seven day dosing schedule).

FIG. 9A illustrates the in vivo effect on viable splenocytes and bone marrow cells of severely immunocompromised mice treated with CV crude extract administered orally (14 day dosing schedule). FIG. 9B illustrates the ex vivo proliferative effect on viable splenocytes of severely immunocompromised mice treated with CV crude extract administered orally (14 day dosing schedule). FIG. 9C illustrates the ex vivo proliferative effect on viable bone marrow cells of severely immunocompromised mice treated with CV crude extract administered orally (14 day dosing schedule).

FIG. 12A illustrates the in vivo effect on viable splenocytes and bone marrow cells of normal mice treated with CV crude extract administered orally (30 day dosing schedule). FIG. 12B illustrates the ex vivo proliferative effect on viable splenocytes of normal mice treated with CV crude extract administered orally (30 day dosing schedule). FIG. 12C illustrates the ex vivo proliferative effect on viable bone marrow cells of normal mice treated with CV crude extract administered orally (30 day dosing schedule).

FIG. 18A is a chromatogram illustrating the molecular weight distribution of CV crude extract. FIG. 18B is a chromatogram illustrating the molecular weight distribution of components of CV crude extract that permeate the Caco-2 cell monolayer.

FIG. 19A is a chromatogram illustrating the molecular weight distribution of CV partially purified extract, C1D5E8. FIG. 19B is a chromatogram illustrating the molecular weight distribution of components of C1D5E8 extract that permeate the Caco-2 cell monolayer.

FIG. 20A is a chromatogram illustrating the molecular weight distribution of CV partially purified extract, C1D5E7. FIG. 20B is a chromatogram illustrating the molecular weight distribution of components of C1D5E7 extract that permeate the Caco-2 cell monolayer.

FIG. 21A is a chromatogram illustrating the molecular weight distribution of CV partially purified extract, C1D5EX. FIG. 21B is a chromatogram illustrating the molecular weight distribution of components of C1D5EX extract that permeate the Caco-2 cell monolayer.

FIG. 23A illustrates the in vivo effect on viable splenocytes of immunocompromised mice treated with CV partially purified extract administered i.p. (3 day dosing schedule). FIG. 23B illustrates the in vivo effect on viable bone marrow cells of immunocompromised mice treated with CV partially purified extract administered i.p. (3 day dosing schedule).

FIG. 24A illustrates the in vivo effect on viable splenocytes of immunocompromised mice treated with CV partially purified extract administered orally (7 day dosing schedule). FIG. 24B illustrates the in vivo effect on viable bone marrow cells of immunocompromised mice treated with CV partially purified extract administered orally (7 day dosing schedule).

DETAILED DESCRIPTION OF THE INVENTION

I. Definitions

Figure 1:
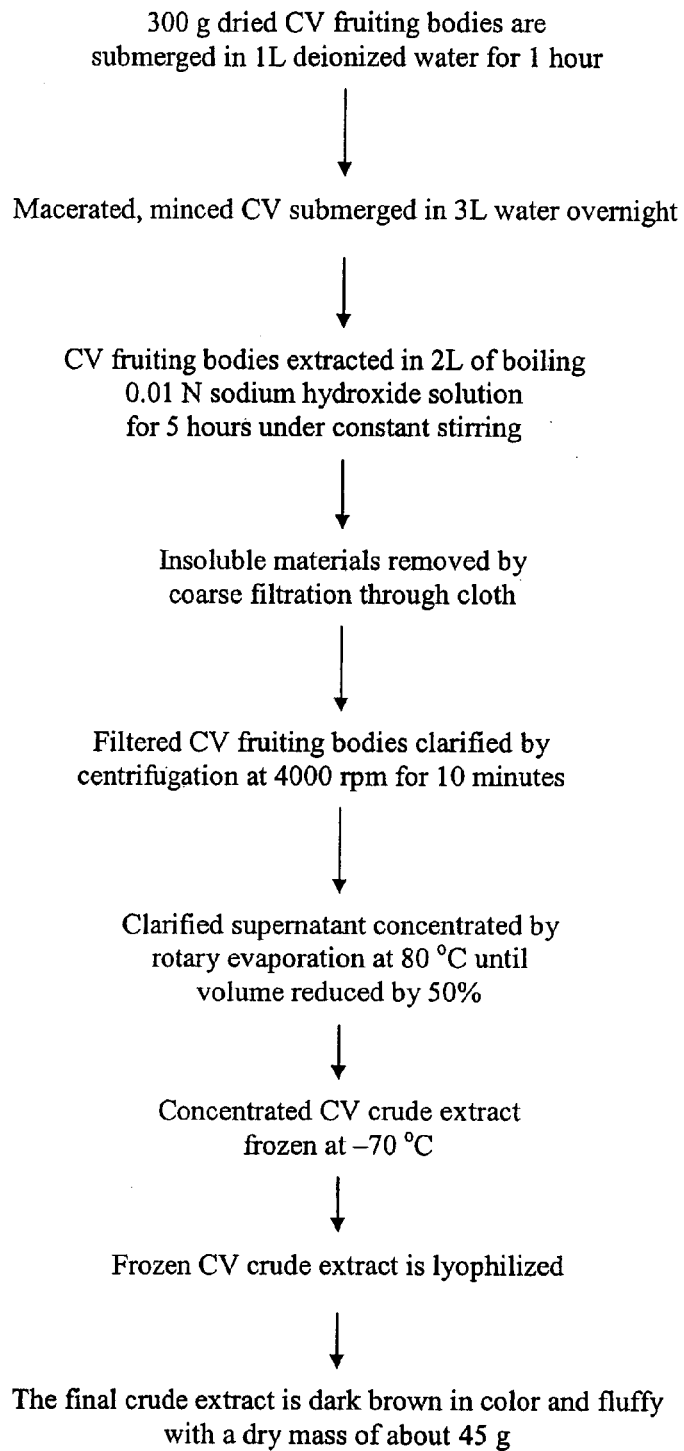
FIG. 1 is a flow chart illustrating the steps used in a protocol for the preparation of CV crude extract.

For purposes of the present invention, the following terms are defined below:

"Immunostimulants", "Immunostimulating agents", and "Immunomodulating agents", as used herein, refer to an agent that induces an immune response.

"Immunogen" refers to an agent or substance capable of provoking an immune response or producing immunity.

"Immunogenicity" refers to the capacity of an immunogen to induce an immune response.

"Immunodeficiency" refers to any deficiency in the capacity to respond immunologically, as by defective production of humoral or cell mediated immunity.

"Immunocompetence" refers to the capacity to respond immunologically to an antigen or immunogen.

"Non-specific immunity" refers to the resistance to the invasion of pathogen resulting from any mechanism other than the formation of antibodies and the generation of specific antigen-reactive lymphocytes.

"Peptide" refers to any substances composed of amino acid residues joined by amide bonds.

"Polysaccharide" refers to a class of carbohydrate in which the molecules results from the polymerization of monosaccharide subunits. A polysaccharide usually contains 5 or more monosaccharide subunits, joined to each other by glycosidic links.

"Glucan" refers to a polysaccharide consisting of glucose.

The term "immune-mediated" refers to a process that is either autoimmune or inflammatory in nature.

An active component of an extract or composition is one that stimulates the immune system.

The term "leukocyte" means a white blood cell. Lymphocytes, monocytes and macrophages are examples of leukocytes.

The term "lymphocyte" refers to a mononuclear leukocyte that mediate humoral or cellular immunity.

The term "monocyte" refers to a mononuclear phagocytic leukocyte that circulates briefly in the bloodstream before migrating into the tissues where it becomes a macrophage.

"T cell" refers to a lymphocyte that matures in the thymus and expresses a T-cell receptor, CD3 and CD4 or CD8. There are several recognized T-cell subpopulations.

"Patient" includes human and other mammalian subjects that receive either prophylactic or therapeutic treatment.

The term "isolated," "purified" or "substantially pure" means an object species that has been enriched or separated from the components in its native environment. Thus, a peptide-linked glucan in an extract is isolated notwithstanding that it may be present together with other peptide-linked glucans or other cellular components. The term may also indicate the an object species is the predominant macromolecular species present (i.e., on a molar basis it is more abundant than any other individual species in the composition), and preferably the object species comprises at least about 50 percent (on a molar basis) of all macromolecular species present. Generally, an isolated, purified or substantially pure composition will comprise more than 80 to 90 percent of all macromolecular species present in a composition. Most preferably, the object species is purified to essential homogeneity (i.e., contaminant species cannot be detected in the composition by conventional detection methods) wherein the composition consists essentially of a single macromolecular species.

All quantitative values include a margin of error representing typical experimental error in measurement of the quantity.

II. General

The present invention provides purified extracts of *Coriolus versicolor* (CV) and active components thereof, methods for purifying the same, and methods for using the same to stimulate immune responses. The active components of the purified extracts of the invention are one or more peptide-linked glucans of low molecular weight (0.7 kDa to 5 kDa and preferably 0.7 kDa to 3 kDa). The peptide-linked glucans retain the immunostimulatory properties of crude extracts of CV that have been widely promoted in the Chinese community as an aid to improve health and to bring longevity upon regular consumption. Recently, traditional extracts have been more commonly used for treating general immune weakness and tumors. Significant improvement in both immune and health status has been observed in cancer patients receiving surgery, chemotherapy and/or radiotherapy after prolonged oral administration of traditional CV extract.

The extract, peptide-linked glucans, and active components thereof of the invention are useful for stimulating immune responses in patients and in vitro in a similar manner to cruder extracts of CV as traditionally practiced in Chinese medicine. Further, the present application provides data indicating that the peptide-linked glucans of the invention can be taken up through the intestinal wall allowing for oral administration as with the cruder extracts of traditional Chinese medicine. However, the extracts and peptide-linked glucans, and active components thereof of the invention have the advantage of greater purity, greater potency and/or greater reproducibility. The extracts, peptide-linked glucans, and active components thereof of the invention can also be used still for further isolation. For example, the data presented in the Examples suggest that the peptide moiety(ies) of the peptide-linked glucans have the principal immunostimulatory activity, although the glucan moiety may confer additional immunostimulatory activity. Thus, the extracts and peptide-linked glucans can be used to prepare isolated peptides and active fragments thereof.

Although an understanding of mechanisms is not required for practice of the invention, it is believed that the mode of action apparently involves proliferation of the lymphocytes and bone marrow cells and activation of macrophages.

III. Purified Extracts and Peptide-Linked Glucans of the Invention

Purified extracts of the invention comprises at least one peptide-linked glucan having a molecular weight of 0.7 kDa to 5 kDa as determined by size exclusion chromatography. The at least one peptide-linked glucan has an immune stimulating activity. The immune stimulating activity can be measured by a statistically significant response in any of the assays described below or in the Examples.

Preferably, the purified extracts of the invention are comprised of at least 50% peptide-linked glucans having a molecular weight of 0.7 kDa to 5 kDa. Some purified extracts of the invention are comprised of at least 60% peptide-linked glucans having a molecular weight of 0.7 kDa to 5 kDa. Some purified extracts of the invention are comprised of at least 70% peptide-linked glucans having a molecular weight of 0.7 kDa to 5 kDa. Some purified extracts of the invention are comprised of at least 80% peptide-linked glucans having a molecular weight of 0.7 kDa to 5 kDa. Some purified extracts of the invention are comprised of at least 85% peptide-linked glucans having a molecular weight of 0.7 kDa to 5 kDa. Some purified extracts of the invention are comprised of at least 90% peptide-linked glucans having a molecular weight of 0.7 kDa to 5 kDa. Some purified extracts of the invention are comprised of at least 99% peptide-linked glucans having a molecular weight of 0.7 kDa to 5 kDa.

The glucan component of the peptide linked glucan comprises glucose molecules linked by a 1–3 linkage. Some extracts contains several peptide-linked glucans, whereas others contain a single-peptide linked glucan. In extracts containing several peptide-linked glucans, the peptide moiety can be the same or different in different peptide-glucans as can the glucan moiety. In preferred extracts, the average molecular weight of peptide-linked glucans is 0.7 to 3 kDa. In some extracts, the average molecular weight of peptide-linked glucans is 0.7 kDa or 1.0 kDa. Molecular weights of no more than 3 kDa are advantageous to ensure passage through the intestinal wall. Some peptide-linked glucans of the invention are further characterized by solubility in water, ethanol and acetone, insolubility in chloroform and dichloroform and lack of hygroscopicity.

IV. Preparation of Purified Extracts and Peptide-linked Glucans of the Invention 1. Preparation of an Active Aqueous Extract of *Coriolus versicolor*

As shown by the flow chart in FIG. 1, an active aqueous extract of CV can be prepared from the dried fruiting bodies of CV by extracting the fruiting bodies with a liquid solvent and concentrating the resulting solution to form a concentrated extract. In some methods, dried fruiting bodies of CV is macerated, depigmented, and boiled in a diluted alkaline aqueous solution such as 0.01 N sodium hydroxide solution. Other alkaline solution such as potassium hydroxide can also be used. Under this heating condition, the concentration of these alkaline aqueous extractants is preferably under 0.1 N to avoid possible loss of activity. After extraction, insoluble materials are removed, for example, by filtration, and the remaining product is clarified by centrifugation or other means. The cleared supernatant is concentrated and lyophilized before storage and use.

The lyophilized supernatant is characterized by a peptide composition of about 4–6%, preferably 4.7% by weight (within experimental error) as determined by a Bradford assay. Preferred extracts have a glucose compound that is 50–60% (preferably 55%) by weight as determined by the phenol sulfuric acid method. Preferred extracts have a uronic acid compound that is about 4–6% by weight, preferably about 4.8%.

2. Preparation of Purified or Partially Purified Active Fractions of CV Extract

Figure 15:
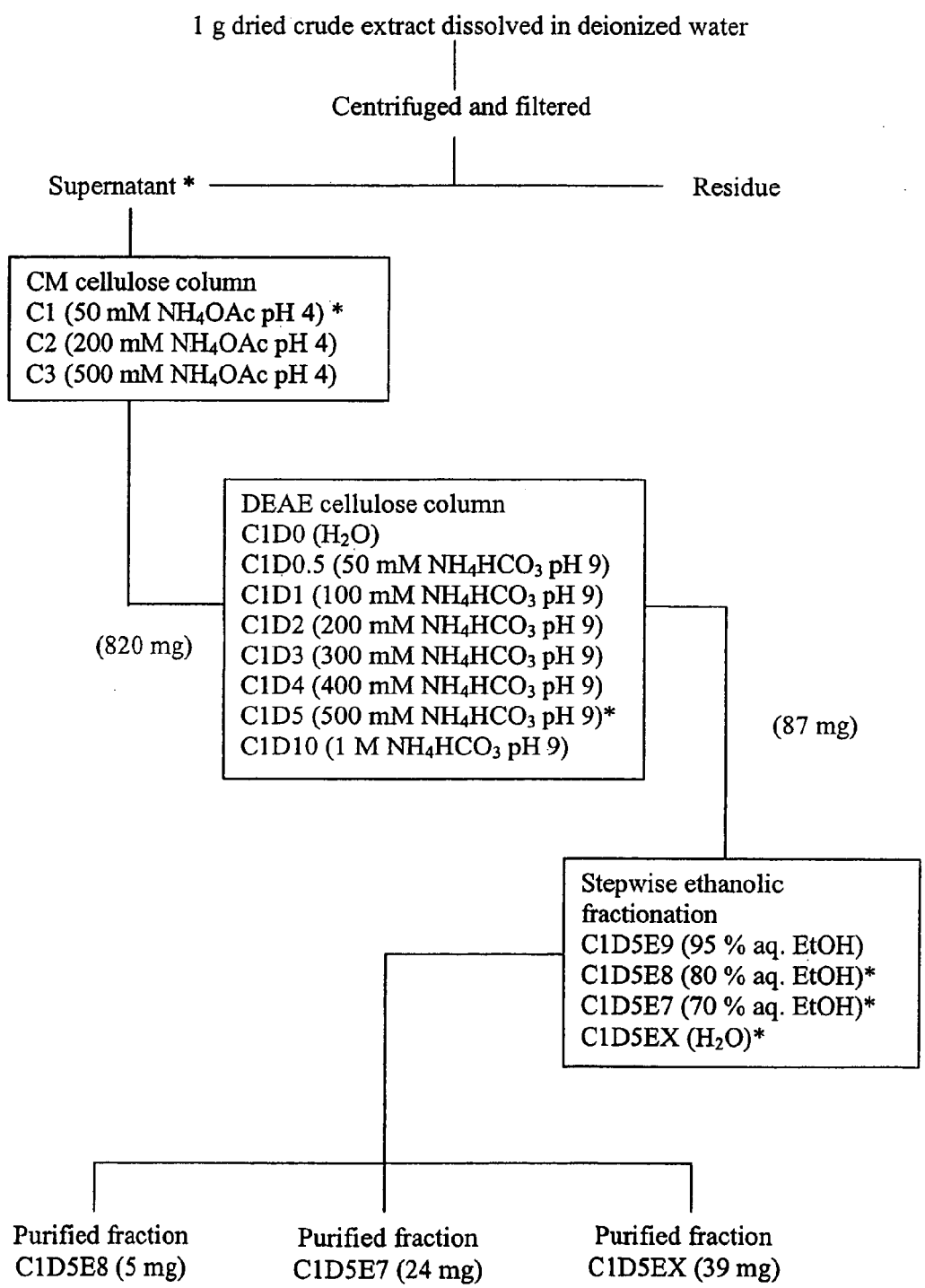
FIG. 15 is a flow chart illustrating steps used in a protocol for further purification of the active components in the crude CV extract of FIG. 1.

The flow chart in FIG. 15 shows an exemplary method for preparing partially purified extracts. The dried crude CV extract is dissolved in water and the less water-soluble substances are removed by centrifugation. Cationic substances of the water-soluble CV extract at pH 4 can be adsorbed and removed by a cationic exchange resin. The active components can then be further purified by any technique that is selective towards the negatively charged molecules. Preferably, the anion exchange resin, DEAE cellulose, was used. The partially purified fractions can be further fractionated by stepwise ethanolic fractionation or gel filtration that separates molecules based on their molecular weights. The preferred molecular weight range is 0.7–3 kDa. In a five-step ethanol gradient, active fractions were isolated from all steps except 95% aqueous ethanol-soluble substances. Further purification can be achieved using some standard methods known in the art such as chromatography. For example, the glucan-moiety of peptide-linked glucans can be separated from the peptide moiety by treatment with a peptidase. The peptide can be separated from the glucan moiety by treatment with a glucanase. Fragments of peptides of peptide-linked glucans can be prepared by selected proteolytic digestion. Individual peptide-linked glucans can be separated by gel electrophoresis, optionally, in two dimensions and excising separated bands.

V. Methods for Determining Immune Stimulating Activity of Purified Extracts and Active Components Immune stimulating activity has different effects on different cell types. For premature immune cells, when challenged by immunostimulating agents, a series of biochemical events occur including increased synthesis of phospholipids and increased permeability of divalent cations. Synthesis of protein, RNA, and finally DNA occurs shortly thereafter. It is the last phenomenon, the increase in DNA synthesis (which eventually results in cell division) that forms the quantitative basis for measurement of lymphocyte and bone marrow cell activation. DNA synthesis is measured by pulse-labeling of the cultures with tritiated thymidine ($^3$H-Tdr), a nucleoside precursor that is incorporated into newly synthesized DNA. The amount of $^3$H-Tdr incorporated relative to the rate of DNA synthesis is determined by scintillation counting. Scintillation counting yields data in counts per minutes (CPM) which are commonly used as a standard measure of the mitogenic responsiveness. The CPMs of the stimulated culture are normalized by CPMs measured in control culture to yield a ratio called the stimulation index.

Effector immune cells such as macrophages are capable of secreting cytotoxic mediators (e.g. $NO^-$) and cytokines (e.g. interleukins and tissue necrotic factors) when activated by immunostimulants. Since macrophages secrete $NO^-$ only upon immunogenic stimulation, the increase of $NO^-$ production by macrophage is commonly used as a method for quantifying the immunostimulatory activity of an immunogen. During incubation with the immunostimulating agents, the highly reactive $NO^-$ produced by the macrophages will quickly be oxidized to the more stable nitrite ($NO_2^-$). The amount of nitrite ion in the supernatant of the culture can then be measured by Griess reaction.

Immune stimulating activity can also be measured in in vivo models of immunity. These models have the advantage of integrating the immune response at the level of the whole animal. Available models to assess the in vivo effect on immunity include examination of cellularity (the number of viable constituent cells) of important immune organs and the delayed-type hypersensitivity. The most recent trend in immunological research has been towards a greater emphasis on the use of ex vivo lymphocyte proliferative responses to demonstrate immune responsiveness[3,4]. Ex vivo assays take advantage of the capacity of cultured lymphocytes to proliferate since in vitro proliferation is a well-recognized property of lymphocytes and has been shown to be a good correlate of host immunity. At the end of the drug treatment, animals are killed to collect immunocompetent cells. Cells are then cultured in vitro for a certain period of time and the cellular uptake of the titrated thymidine is assessed. Although most immunocompetent cells can proliferate when cultured, proliferation has to be enhanced with immunostimulants e.g. Con A and LPS to achieve measurable levels[3].

Delayed-type hypersensitivity reactions are good correlates of cell-mediated immunity. Contact hypersensitivity is one kind of delayed-type hypersensitivity; antigens, essentially a hapten, on the skin surface is taken, processed and presented by Langerhans cells to T CD4$^+$ lymphocytes that eventually lead to vasodilatation and swelling of ear. Potent contact sensitizers, such as dinitrofluorobenzene (DNFB), are used to induce a contact sensitivity reaction in mice, the intensity of which can be regulated by treating the animals with drugs or exposing them to chemicals. Ear thickness is measured immediately before sensitization and 24 hours later using a digital caliper. The increase in ear thickness is a good indicator of delayed-type hypersensitivity[3].

Immune stimulating activity can also be measured on patients in clinical and preclinical studies, which indicated that the ability of immunostimulants to potentiate the clinical efficacy of conventional cancer treatment, to restore immune functions from immunocompromised status and to enhance resistance to infections is primarily due to their non-specific stimulation of the immunological defense system[2]. Non-specific immunity can be boosted by antigen or, more directly, immunogen. At the molecular level, immunogen, which possesses special structural units termed antigenic determinant, can cross-link the surface receptors of certain immune cells, leading to clonal expansion or activation.

An extract or peptide-linked glucan or active component thereof of the invention has immune stimulating activity when it elicits a statistically significant response in one of the above assays. Often the response to the extract or peptide-linked glucan or active component is compared with that of a control or placebo.

VI. Intestinal Permeability

Purified extracts, peptide-linked glucans of the invention and active components thereof can also be screened for permeability through the intestine. Such is advantageous in allowing oral administration. Screening can be performed using a Caco-2 cell line, a well-differentiated human intestinal cell line derived from colorectal carcinoma, which has been rigorously validated as a surrogate of intestinal epithelial cells for studying intestinal absorption in vitro. A good correlation between the bioavailability in humans and the permeability results obtained with Caco-2 monolayer in Transwell® insert has been established. The molecular weight distribution and immunogenicity of the components capable of transporting across the Caco-2 monolayer can be characterized by size exclusion chromatography and the bioassays described above[5,6]. Permeability can also be measured in in vivo animal models.

VII. In Vitro Methods on Cellular Responses

CV extract, peptide-linked glucan or active components can be used in a number of in vitro or ex vivo methods. In some methods, cellular responses to these agents are analyzed to provide information to optimize dosage regimes of these agents in vivo. In some methods, CV extract, peptide-linked glucan or active components are used as positive controls to screen other drugs for effects on splenocyte or bone marrow cell proliferation or macrophage secretion. If the positive control stimulates proliferation of the splenocytes or bone marrow cells or secretion of the macrophage, whereas a candidate drug does not in a parallel reaction, then it can be concluded that the test drug is ineffective. In other methods, proliferating PMB's are obtained from a patient with an immune disorder. The lymphocytes are treated with CV extract, peptide-linked glucan or active components ex vivo and then returned to the patients. As with other agents that stimulate the immune system, such as ConA or LPS, CV extract, peptide-linked glucan or active components can also be marketed as scientific reagents to the research community to investigate the activated state of cells or be used as controls to discover other agents that stimulate the immune system.

VIII. Patients Amenable to Treatment

Patients amenable to treatment include individuals at risk of immunodeficiency, but are not yet immunodeficient, as well as patients presently suffering from immunodeficiency. Immunodeficiency results in enhanced susceptibility to opportunistic infections. Thus, patients treated with CV extracts or peptide-linked glucans or active components thereof have decreased susceptibility to opportunistic infections.

The methods are particularly suitable for treating secondary immunodeficiency that results from a primary condition. In some disorders the secondary immunodeficiency may be transient and patients may become immunocompetent with adequate treatment of the primary disease, e.g., tuberculosis, leprosy. In other conditions, the secondary immunodeficiency may become permanent, e.g. congenital rubella. Thus, treatment regimes may vary based on the primary condition. A variety of disorders are associated with secondary immunodeficiency; secondary immunodeficiency may result from an infection, a malignant neoplastic disease, an autoimmune disease, a protein losing state, an immunosuppressive treatment, surgery, or anesthesia.

Infections that can result in secondary immunodeficiency include: rubella, congenital rubella; measles; leprosy, tuberculosis, coccidioidomycosis, chronic infection, acute viral infection, cytomegalovirus, multiple viral infection, and repeated viral infections.

Malignant neoplastic diseases that can result in secondary immunodeficiency include: Hodgkin's disease, acute leukemia, chronic leukemia, nonlymphoid cancer, and myeloma.

Autoimmune diseases that can result in secondary immunodeficiency include: systemic lupus erythematosus (SLE), rheumatoid arthritis, and chronic active hepatitis.

Protein losing states that can result in secondary immunodeficiency include: nephrotic syndrome and protein-losing enteropathy.

Immunosuppressive treatments that can result in secondary immunodeficiency include: corticosteroids, cytotoxic drugs, alkylating agents, antimetabolites, antithymocyte globulin, radiation, cyclosporine, phenytoin, and penicillamine.

Other conditions that can result in secondary immunodeficiency include: diabetes, alcoholic cirrhosis, malnutrition, burns, sarcoidosis, splenectomy, sickle cell disease, uremia, aging, subacute sclerosing panencaphalitis, Down's syndrome, newborns, and premature infants.

VIII. Therapeutic Methods, Pharmaceutical Compositions and Methods of Administration A. Therapeutic Methods In prophylactic application, pharmaceutical compositions or medicaments are administered to a patient susceptible to, or otherwise at risk for developing an immune disorder in an amount sufficient to prevent, reduce, or arrest the development of an immune disorder. In therapeutic applications, compositions or medicaments are administered to a patient suspected to develop, or already suffering from an immunological disease in an amount sufficient to reverse, arrest, or at least partially arrest, the symptoms of an immune disorder. In both prophylactic and therapeutic regimes, the *Coriolus versicolor* extract or peptide-linked glucan or active component of the present invention are usually administered in several dosages until a sufficient response has been achieved. However, in both prophylactic and therapeutic regimes, the extract, peptide-linked glucan or active component or the CV partially purified extract of the present invention can be administered in a single dosage until a sufficient response has been achieved. Typically, the treatment is monitored and repeated dosages can be given. Furthermore, the treatment regimes can employ similar dosages, routes of administration, and frequency of administration to those used in treating other immune-mediated disorders.

The amount of CV extract, peptide-linked glucan or active component thereof that can be combined with a carrier material to produce a single dosage form may vary depending upon the disease treated, the mammalian species, and the particular mode of administration. The "effective dosage", "pharmacologically acceptable dose" or "pharmacologically acceptable amount" for any particular patient can depend on a variety of factors including the activity of the specific compound employed, the species, age, body weight, general health, sex and diet of the patient being treated; the time and route of administration; the rate of metabolism or excretion; other drugs which are concurrently or have previously been administered; the type and severity of the immunological disease; severity of side-effects, whether the patient is animal or human, and the like. Usually the patient is human, but nonhuman mammals, including transgenic mammals, can also be treated.

For any extract, peptide-linked glucan or active component used in the methods of the present invention, an effective dose for humans can be estimated initially from non-human animal models. An effective dose can be determined by a clinician using parameters known in the art. Generally, dosing begins with an amount somewhat less than the optimal effective dose. Dosing is then increased by small increments thereafter until an effective dosage is achieved. (See *The Merck Manual of Diagnosis and Therapy*, 16$^{th}$ Edition, § 22, 1992, Berkow, Merck Research Laboratories, Rahway, N.J., which is incorporated herein by reference).

Dosages need to be titrated to optimize safety and efficacy. Toxicity and therapeutic efficacy of the compounds described herein can be determined by standard pharmaceutical procedures in experimental animals, e.g., by determining the $LD_{50}$, (the dose lethal to 50% of the population tested) and the $ED_{50}$ (the dose therapeutically effective in 50% of the population tested). The dose ratio between toxic and therapeutic effect is the therapeutic index and can be expressed as the ratio between $LD_{50}$ and $ED_{50}$. Compounds which exhibit high therapeutic indices are preferred. The data obtained from these nonhuman animal studies can be used in formulating a dosage range that is not toxic for use in humans. The dosage of such compounds lies preferably within a range of circulating concentrations that include the $ED_{50}$ with little or no toxicity. The exact formulation, route of administration and dosage can be chosen by the individual physician in view of the patient's condition. (See, e.g., Fingl et al. (1975) In: *The Pharmacological Basis of Therapeutics*, Chapter 1, which is incorporated herein by reference).

In some methods the CV extract, peptide-linked glucan or active component is administered orally at a dosage of 1.0 mg to 1000 mg/kg per day, preferably at a dosage of 20 mg/kg to 50 mg/kg of body weight per day. In other methods, the CV extract, peptide-linked glucan or active component is administered orally at a dosage of 0.001 mg to 100 mg/kg per day. The CV extract, peptide-linked glucan or active component can be administered as a single daily dose or as multiple daily doses. In some methods, the CV extract, peptide-linked glucan or active component thereof is administered orally at a daily dosage equivalent to at least 50 mg of CV crude extract per kg of body weight per day.

B. Pharmaceutical Compositions and Methods of Administration

CV extract, peptide-linked glucan and active components thereof can be delivered or administered to a mammal, e.g., a human patient or subject, alone, in the form of a pharmaceutically acceptable salt or hydrolyzable precursor thereof, or in the form of a pharmaceutical composition wherein the compound is mixed with suitable carriers or excipient(s) in an effective dosage. Solid oral dosages are the preferred pharmaceutical composition. An effective regime means that a drug or combination of drugs is administered in sufficient amount and frequency and by an appropriate route to at least detectably prevent, delay, inhibit or reverse development of at least one symptom of an immunological disorder. An "effective dosage", "pharmacologically acceptable dose", "pharmacologically acceptable amount" means that a sufficient amount of CV extract, peptide-linked glucan or active component thereof to achieve a desired result, e.g., stimulating an immune response, preventing, delaying, inhibiting or reversing a symptom of an immune disorder or the progression of an immune disorder when administered in an appropriate regime.

CV extract, peptide-linked glucan or active components thereof that are used in the methods of the present invention can be administered as pharmaceutical compositions alone, together, and/or with a variety of other pharmaceutically acceptable components. Pharmaceutical compositions can be in the form of solids (such as powders, granules, dragees, tablets or pills), semi-solids (such as gels, slurries, or ointments), liquids, or gases (such as aerosols or inhalants).

Suitable formulations for use in the present invention are found in *Remington's Pharmaceutical Sciences* (Mack Publishing Company 1985) Philadelphia, Pa., 17$^{th}$ edition) and Langer, *Science* (1990) 249:1527–1533, which are incorporated herein by reference. The pharmaceutical compositions described herein can be manufactured in a conventional manner, i.e., mixing, dissolving, granulating, dragee-making, levigating, emulsifying, encapsulating, entrapping or lyophilizing processes.

CV extract, peptide-linked glucan or active components can be formulated with common excipients, diluents or carriers, and compressed into tablets, or formulated as elixirs or solutions for convenient oral administration. CV extract, peptide-linked glucan or active components can also be formulated as sustained release dosage forms and the like. Administration of the compounds can be achieved in various ways, including oral, buccal, rectal, parenteral, intraperitoneal, intradermal, transdermal, intratracheal, intravenous, subcutaneous, and intramuscular administration. Oral administration is preferred. The compound can be administered in a local rather than systemic manner, in a depot or sustained release formulation. In addition, the compounds can be administered in a liposome. Further, the compounds may be combined with food and eaten, or combined with consumable liquids and drunk as a beverage.

For oral administration, the compounds can take the form of pills, tablets, capsules, powders, or granules formulated in a conventional manner. For oral administration, the compositions can be in liquid form, e.g., solutions, suspensions or emulsions.

For buccal administration, the compounds can take the form of tablets or lozenges formulated in a conventional manner.

For administration by inhalation, the compounds for use according to the present invention are conveniently delivered in the form of an aerosol spray preparation from pressurized packs, a nebulizer or a syringe sprayer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oil-based or aqueous vehicles, and can contain formulation agents such as suspending, stabilizing and/or dispersing agents. The compositions for parenteral administration are formulated as sterile, substantially isotonic and in full compliance with all Good Manufacturing Practice (GMP) regulations of the U.S. Food and Drug Administration.

CV extract, peptide-linked glucan or active components can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, CV extract, peptide-linked glucan or active components can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, for example, as a sparingly soluble salt. (See, e.g., Urquhart et al., (1984), *Ann Rev. Pharmacol. Toxicol.* 24:199; Lewis, ed., 1981, *Controlled Release of Pesticides and Pharmaceuticals,* Plenum Press, New York, N.Y., U.S. Pat. Nos. 3,773,919, and 3,270,960, which are incorporated herein by reference).

Alternatively, other delivery systems for hydrophobic pharmaceutical compounds can be employed. Liposomes and emulsions are well known examples of delivery vehicles or carriers for hydrophobic drugs. In some methods, long-circulating, i.e., stealth liposomes can be employed. Such liposomes are generally described in Woodle, et al., U.S. Pat. No. 5,013,556, the teaching of which is hereby incorporated by reference. The compounds of the present invention can also be administered by controlled release means, sustained release means, and/or delivery devices such as those described in U.S. Pat. Nos. 3,845,770; 3,916,899; 3,536,809; 3,598,123; and 4,008,719; the disclosures of which are hereby incorporated by reference.

The pharmaceutical compositions also can comprise suitable solid or gel phase carriers or excipients. Examples of such carriers or excipients include calcium carbonate, calcium phosphate, various sugars, starches, cellulose derivatives, gelatin, and polymers such as polyethylene glycols.

XI. EXAMPLES

The following examples are provided by way of illustration, and not by way of limitation. Thus, selection of reagents, as well as concentration of reagents, temperatures, and other variable parameters are used to exemplify application of the present invention and are not to be considered as limitations thereof. Those of skill in the art will readily recognize non-critical parameters which can be varied to accomplish the invention described herein.

Example I

Preparation of the *Coriolus versicolor* Crude Extract

The *Coriolus versicolor* (CV) crude extract is prepared by performing the following steps. The dried *Coriolus versicolor* (CV) fruiting bodies are macerated. The macerated CV fruiting bodies are then minced. A step to remove pigment from the macerated, minced CV fruiting bodies may be performed. Next, the CV fruiting bodies are extracted. The extraction may be accomplished by boiling the CV fruiting bodies in an aqueous alkaline solution, e.g., sodium hydroxide or potassium hydroxide. An aqueous alkaline solution of less than 0.1 N is preferred. Following the extraction step, the preparation of the crude CV extract may include one or more of the following steps: removing the insoluble materials, e.g., by filtration; clarifying the extract, e.g., by centrifugation; concentrating the extract, e.g., by rotary evaporator, freezing the extract, or lyophilizing the extract, e.g., by freeze dryer. The resulting crude CV extract may then be used or stored for later use.

FIG. 1 is a flow chart which illustrates the steps of a protocol for the preparation of CV crude extract. 300 g of *Coriolus versicolor* (CV) dried fruiting bodies are macerated by submersion in 1 L deionized water for about one hour. After decanting the deionized water, the macerated CV fruiting bodies are minced. Pigment may be removed from the macerated, minced CV fruiting bodies. Pigment removal is to be accomplished by submerging the macerated, minced CV fruiting bodies in 3 L of deionized water overnight. Extraction of the CV fruiting bodies is performed by boiling the macerated, minced CV fruiting bodies in 2 L of 0.01 N sodium hydroxide for five hours under constant gentle stirring.

The insoluble materials are removed by pouring the extract through a coarse cloth which traps the insoluble materials. The resulting supernatant is clarified by centrifugation at 4000 rpm for 10 minutes. The clarified supernatant is then concentrated by rotary evaporation at 80° C. until the volume is reduced by 50%. Next, the clarified, concentrated supernatant is frozen at −70° C. and lyophilized. The resulting crude CV extract has dry mass of around 43 g to 47 g, is dark brown in color, and has a fluffy texture. The crude CV extract may be used immediately or stored for later use.

Example II

Physical and Chemical Characteristics of Crude CV Extract

CV crude extract was analyzed to estimate its solubility, melting point, degradation temperature, and hygroscopicity. The methods used for the analysis and the respective results are presented in Table I.

TABLE I

| Results | Method(s) |
| --- | --- |
| Highly soluble in water | Dissolve 10 mg of CV extract in 2 ml solvent (water) in a glass test tube. Sonicate for 30 minutes. Measure the absorbance at 254 nm. |
| Moderately less soluble in ethanol than in water | As described above, except solvent is ethanol. |
| Moderately less soluble in acetone than in water | As described above, except solvent is acetone. |
| Insoluble in chloroform | As described above, except solvent is chloroform. |
| Insoluble in dichloromethane | As described above, except solvent is dichloromethane. |
| No defined melting point temperature | 1. Differential scanning calorimetry A Perkin Elmer Pyris 1 differential scanning calorimeter (with Pyris Manager software) was employed. The sample was placed inside a hermetically sealed aluminum pan and scanned from 40° to 90° C. at a heating rate of 10° C./min under nitrogen purge. (See Ford, J. L. and Timmins P. Pharmaceutical Thermal Analysis - Techniques and Applica- |

TABLE I-continued

| Results | Method(s) |
|---|---|
| | tions, Ellis Horwood Ltd., Chichester, West Sussex, England, 1989.) |
| | 2. Thermal gravimetric analysis A Perkin Elmer thermogravimteric analyzer TGA7 with Thermal Analysis Controller TAC 7/DX was employed. The sample was placed in an open pan and scanned from 40° to 110° C. at a heating rate of 10° C./min. (See Ford, J. L. and Timmins P. Pharmaceutical Thermal Analysis - Techniques and Applications, Ellis Horwood Ltd., Chichester, West Sussex, England, 1989.) |
| No defined degradation temperature | 1. Differential scanning calorimetry Performed as described above. 2. Thermal gravimetric analysis Performed as described above. |
| Non-hygroscopic Gravimetric changes observed after incubation at constant relative humidity (RH): <5% increase in weight after incubation at 10–70% RH for 14 days | Chu K. K. W. and Chow A. H. L., Pharm. Res. 2000, 17(9): 1133–1137. |

CV crude extract was analyzed to determine the average molecular weight, and the w/w percentages of neutral sugar, uronic acid, and peptide/protein. CV crude extract was also analyzed for the presence of glucose as a component monosugar and for the presence of (1→3) glucan linkage. The linkage of the peptide moiety with the carbohydrate moiety present in the CV crude extract was characterized. The methods used for the analysis and characterization, and the respective results are presented in Table II.

TABLE II

| Results | Method(s) |
|---|---|
| Average molecule weight: 2.6 kDa Molecular weight range: 0.5–40 kDa | Chromatography |
| Peptide/protein: 4.7% w/w | Bradford assay of Bradford, M. M., Anal. Biochem. 1976, 72: 248–254. |
| Neutral sugar: 55% w/w | Phenol sulfuric acid method of Dubois, M. et al., Anal. Chem., 1956, 28: 350–356. |
| Uronic acid: 4.8% w/w | Carbozole assay of Blumenkrantz, N. et al., Anal. Biochem. 1973, 54: 484–489. |
| Glucose as component monosugar | Acid hydrolysis as determined by the method of Zhang Y. W. et al., 1997, 63(00): 393–399. Alditol acetate derivatization as determined by the method of Kiyohara, H. et al., Carbohydr. Res., 1998, 182: 259–275. Gas chromatography as described by Kiyohara, H. et al., Carbohydr. Res., 1998, 182: 259–275. |
| (1→3) glucan | Methylation as determined by the method of Hakomori, S., J. Biochem. Tokyo, 1964, 55: 205–208. Acid hydrolysis as determined by the method of Zhang Y. W. et al., 1997, 63(00): 393–399. Alditol acetate derivatization as determined by the method of Kiyohara, H. et al. Carbohydr. Res., 1998, 182: 259–275. GC/MS as determined by the method of Kiyohara, H. et al., Carbohydr. Res., 1998, 182: 259–275 |
| Peptide moiety tightly linked with the carbohydrate moiety | Co-elution of the two moieties in different chromatographic analyses |

The average molecular weights of the crude CV extracts were determined by size exclusion chromatography. 200 μl of aqueous samples at 1–2 mg/ml were injected onto a high performance liquid chromatography (HPLC) system (fast performance liquid chromatographic system, Pharmacia), run on a Superose 12 10/30 column, and eluted with 0.2 M NaCl solution pH 7.0. The eluant was then applied to a 2×40 cm Superdex 75 10/30 column and eluted with 200 mM ammonium acetate pH 7.0. The eluant was collected as 1 ml fractions. The fractions were subsequently used as samples for analysis. UV absorbance was monitored at 210 nm throughout the separation process.

The molecular weight of the samples ranged from 0.5–40 kDa. The average molecular weight of samples was 2.6 kDa. Molecular weight was determined by referring to a calibration curve constructed using various carbohydrate standards.

Figure 2A:
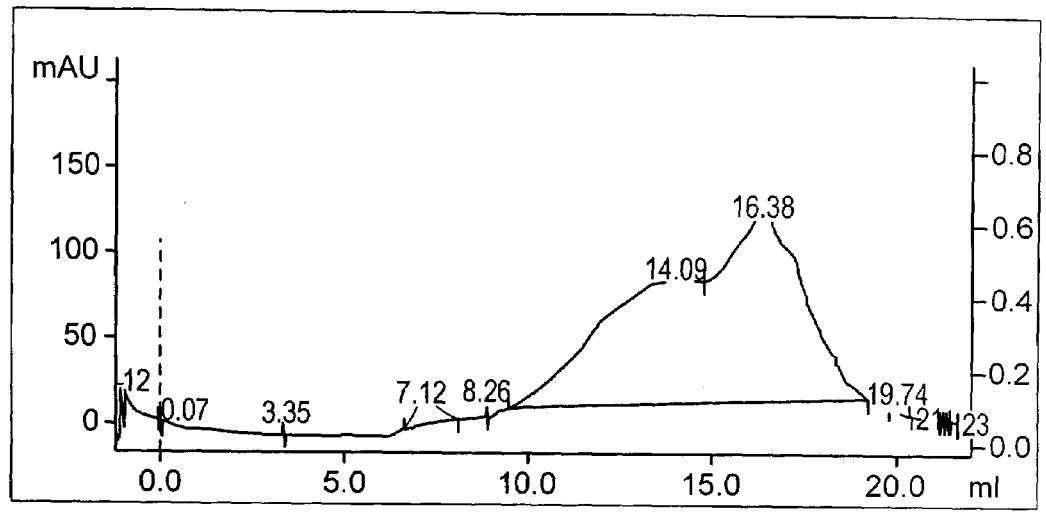
FIGS. 2A and 2B.
Figure 2B:
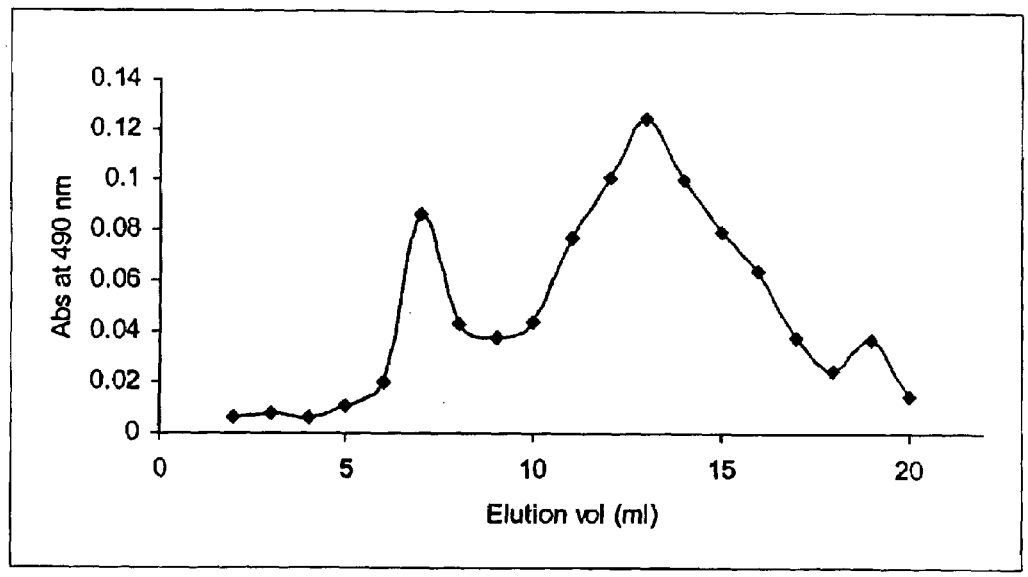

FIG. 2A is a size exclusion chromatogram which shows the elution profile of the protein component of CV crude extract. The protein content in the samples was measured by monitoring the elution profile of the protein-containing substances at 254 nm. (See Table II.) FIG. 2B is a size exclusion chromatogram of CV crude extract which shows the elution profile of the carbohydrate component of CV crude extract. The carbohydrate content in the eluants was measured by the phenol sulfuric acid test. (See Table II.)

In Vitro Studies

Example III

Proliferation of Viable Murine Splenocytes Contacted with CV Crude Extract In Vitro Three ICR mice were sacrificed by cervical dislocation. The spleens of the sacrificed mice were aseptically removed. Splenocytes were isolated by gently pressing each spleen through a stainless steel sieve. The splenocytes isolated from each mouse were pooled, the resulting cell suspension was centrifuged at 1600 rpm for 3 min, and the supernatant was decanted. About 6 ml of lysis buffer was added to the cell pellets to destroy the red blood cells present in the pellet. The residual lysis buffer was subsequently washed away with PBS. The splenocytes were then suspended in complete cell culture medium.

The viability of the cell suspension was assessed by trypan blue exclusion test. (See Parslow T. G. The immune response. In *Medical Immunology;* Sities D. P., Terr A. I., Parslow T. G., Eds., Appleton and Lange: London, 1997; pp 63–73.) The cell density of viable cell suspensions was adjusted to 2×10 cells/ml. 100 μl of the cell suspensions were seeded into 96-well microtiter plates (NUNC™).

The seeded cells were then contacted with (1) a 100 μl sample of CV crude extract (at final concentrations of 1–500 μg/ml), (2) 100 μl of Concanavalin A (Con A) (at final concentrations of 0.016–4.0 μg/ml), as a positive control, (Sigma) or (3) 100 μl culture medium as a negative control.

The contacted cells were then incubated at 37° C. in a humidified atmosphere of 95% $O_2$ and 5% $CO_2$ for 72 hrs. At hour 54, the cells were pulsed labeled with 0.5 μCi/10

μl/well of $^3$H-methyl-thymidine. At hour 72, the cells were then harvested onto a glass fiber filter paper with a cell harvester, and the amount of $^3$H-methyl-thymidine incorporated relative to DNA synthesis was determined by scintillation counting. The counts per minute (CPM) of the contacted cells were normalized by the CPMs in the negative control cells to yield the stimulation index. The stimulation index was calculated by dividing the cellular incorporation of $^3$H-methyl-thymidine (counts per min (CPM)) in the contacted cells by that of the negative control cells.

Figure 3:
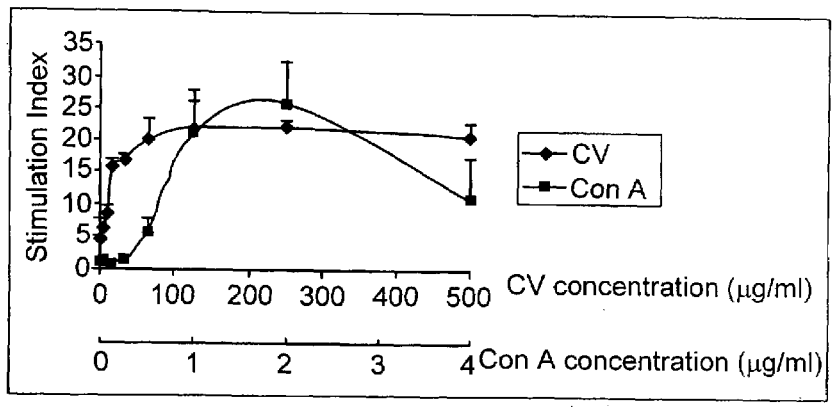
FIG. 3 illustrates the proliferation of viable murine splenocytes contacted with CV crude extract or Concanavalin A (Con A) in vitro.

The proliferative activity of splenocytes from mice treated with CV extract was dose-dependent at low Con A concentrations. The proliferative activity of splenocytes from mice treated with CV extract was 20 fold at a concentration of 50 μg/ml Con A when compared to the control. The proliferative response of splenocytes from mice treated with CV crude extract at concentrations of 100 μg/ml to 350 μg/ml and stimulated with concentrations of about 1 μg/ml to about 3 μg/ml of Con A was similar. The results are expressed as the stimulation index. (See FIG. 3.)

Example IV

Murine Bone Marrow Cells Contacted with CV Crude Extract In Vitro

Five ICR mice were sacrificed by cervical dislocation. The femurs of the sacrificed mice were aseptically removed. The muscles associated with the femurs were cleared as much as possible, and marrow plugs were taken. The marrow plugs were flushed with PBS using a 2 ml syringe fitted with a 25 G needle. The bone marrow cells isolated from each bone marrow plug were pooled. The resulting cell suspension was prepared, and the viability of the cell suspension was tested as described in Example III, above. The density of the viable cell suspensions was adjusted to produce a cell suspension of $4\times10^6$ cells/ml. 100 μl of the cell suspensions were seeded into 96-well microtiter plates (NUNC™).

The cells were then contacted with (1) a 100 μl sample of CV crude (at final concentrations of 25–200 μg/ml), (2) 100 μl of lipopolysaccharide (LPS) (at final concentrations of 2.5–20 μg/ml), as a positive control, (Sigma) or (3) 100 μl culture medium, as a negative control. The contacted cells were incubated for 120 hours at 37° C. in an atmosphere of 95% $O_2$ and 5% $CO_2$. At hour 104, the cells were pulsed labeled with 0.5 μCi/10 μl/well of $^3$H-methyl-thymidine. At hour 120, the cells were harvested and the stimulation index determined as in Example III, above.

Figure 4:
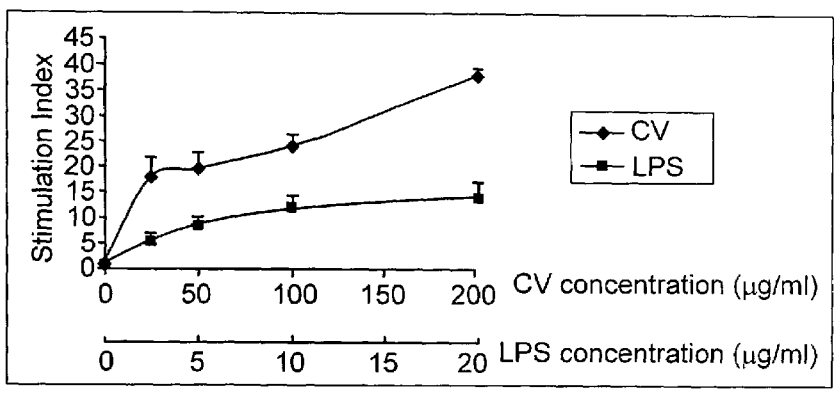
FIG. 4 illustrates the proliferative effect of contacting isolated murine bone marrow cells with CV crude extract or LPS in vitro.

FIG. 4 illustrates the proliferative effect of contacting isolated murine bone marrow cells with CV crude extract or LPS in vitro. The results are expressed as the stimulation index. CV crude extract was shown to proliferate the bone marrow by 40 fold at 200 μg/ml. The proliferative response of bone marrow cells contacted with CV crude extract was greater than the response at similar relative concentrations of LPS.

Example V

Murine Macrophages Contacted with CV Crude Extract In Vitro

Ten ICR mice were injected intraperitoneally with 1 ml 3% w/v aqueous thioglycolate. After 3 days, the mice were sacrificed by cervical dislocation. Macrophages were harvested by opening the peritoneum and lavaging the space with PBS. The PBS lavage from each sacrificed mouse was pooled. The resulting cell suspension was prepared, and the viability of the cell suspension was tested as described in Example III, above. The density of the viable cell suspensions was adjusted to produce a cell suspension of $4\times10^6$ cells/ml. 100 μl of the cell suspensions was seeded into 96-well microtiter plates (NUNC™).

The cells were allowed to adhere on the bottom of the wells of microtiter plates for 1 hr at 37° C. in a humidified atmosphere of 95% $O_2$ and 5% $CO_2$. Next, the supernatant in the wells was carefully removed. The cells were then contacted with (1) 200 μl of CV crude extract in concentrations of 25–200 μg/ml (2), 200 μl of LPS (Sigma) in concentrations of 0.125–1 μg/ml, as a positive control, or (3) 200 μl complete cell culture medium, as a negative control. The contacted cells were incubated at 37° C. in a humidified atmosphere of 95% $O_2$ and 5% $CO_2$ for 24 hours.

At 24 hours, the amount of nitrate present in the cell-free culture medium was determined by the Griess reaction. (See Green L. C. et al, Analysis of nitrate, nitrite, and [15N] nitrate in biological fluids, *Anal. Biochem.*, 1982, 126: 131–138.) A 150 μl aliquot of cell-free culture medium was pipetted from each microtiter plate well, and reacted with 50 μl of Griess reagent for 10 minutes in a fresh microtiter plate well. Absorbance of the aliquot was then measured at 540 nm using a microplate reader (BTI, ELX 800).

Figure 5:
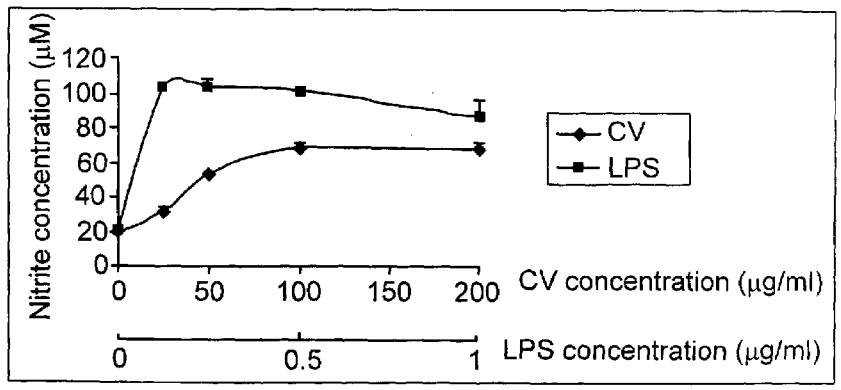
FIG. 5 illustrates the increased secretion of nitric oxide by murine peritoneal macrophages contacted with CV crude extract or LPS in vitro.

FIG. 5 illustrates the increased secretion of nitric oxide by murine peritoneal macrophages contacted with CV crude extract or LPS in vitro. The increased secretion of nitric oxide by proliferative activity of murine peritoneal macrophages treated with CV crude extract was dose-dependent at CV concentrations of less than about 100 μg/ml. There was no increase in proliferative activity of cells contacted with concentrations of more than about 100 μg/ml of CV crude extract. The proliferative activity of LPS was dose-dependent at low LPS concentrations.

In Vivo Studies

Example VI

Administration of CV Crude Extract to Normal Mice

Study Design

Twenty ICR mice were sorted into four groups of 5 mice each. As shown in Table III, Group 1 was treated with CV crude extract administered i.p; Group 2 was treated with normal saline administered i.p., as a negative control; Group 3 was treated with CV crude extract administered orally; and, Group 4 was treated with deionized water administered orally, as a negative control. Oral administration was accomplished by using an intragastric tube to force feed the mice.

Table III shows the dose and dosing schedule of each group. The mice of Group 1 and Group 2 were sacrificed on day 4. The mice of Group 3 and Group 4 were sacrificed on day 8.

On day 1, CV crude extract was weighed and dissolved in deionized water, and the concentration of the solution was adjusted to 5 mg/ml solution. The solution was sonicated for 30 minutes, centrifuged at 4000 rpm for 10 minutes to remove any insoluble material, and then filtered through sterile 0.22 μm filter (IWAKI) into a sterile bottle. The solution was stored at 4° C. between uses.

TABLE III

| Treatment Group | Number of Mice | CV Dose | CV Dosing Schedule | Route of Administration |
|---|---|---|---|---|
| 1 | 5 | 50 mg/kg/day (0.25 ml of 5 mg/ml solution injected into an approximately 25 g mouse) | days 1, 2, & 3 | i.p. injection |
| 2 | 5 | 0.25 ml sterile normal saline pH 7.4 | days 1, 2, & 3 | i.p. injection |
| 3 | 5 | 50 mg/kg/day (0.25 ml of 5 mg/ml solution orally into an approximately 25 g mouse) | On days 1–7 | oral |
| 4 | 5 | 0.25 ml deionized water | On days 1–7 | oral |

Figure 6A:
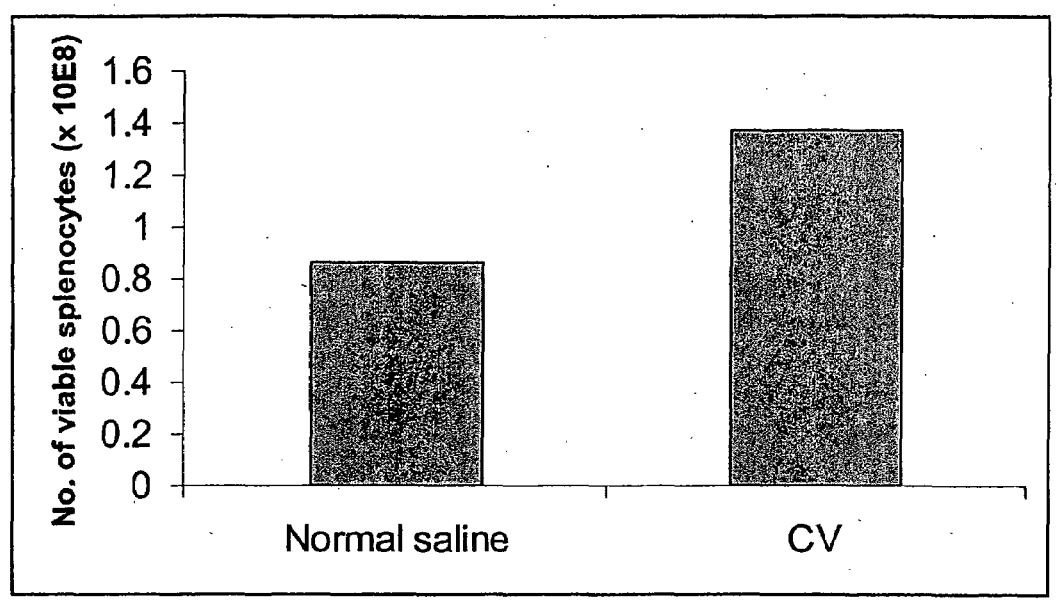
FIGS. 6A and 6B.

1. Effect of i.p. Administration of CV Crude Extract on the In Vivo Proliferation of Viable Murine Splenocytes from Normal Mice CV crude extract administered i.p. to mice (Group 1) increased the number of in vivo viable splenocytes by 58.6% when compared to control mice (Group 2). (See FIG. 6A.) Splenocytes were harvested and isolated as described in Example III, above. The resulting cell suspension was prepared, and the viability of the cell suspension was tested as described in Example III, above.

Figure 6B:
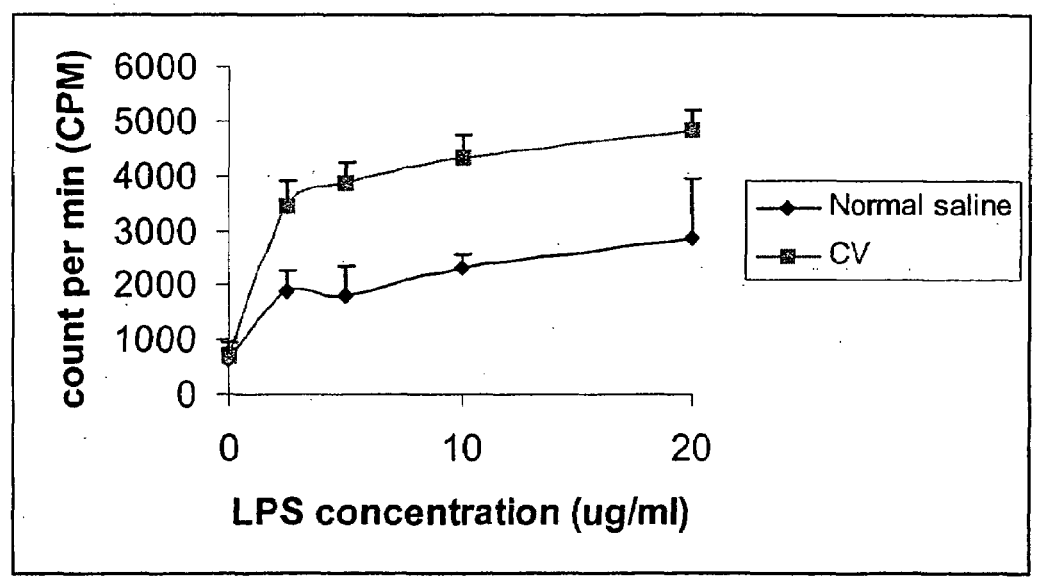

2. Effect of i.p. Administration of CV Crude Extract on the Ex Vivo Proliferation of LPS Stimulated Murine Bone Marrow Cells from Normal Mice The bone marrow cells of mice treated with CV crude extract administered i.p. (Group 1) showed greater ex vivo LPS-stimulated proliferative activity than did the bone marrow cells of the control mice (Group 2). (See FIG. 6B.) The bone marrow cells were harvested and isolated as described in Example IV, above. The proliferative activity of CV crude extract on the bone marrow cells was tested as described in Example IV, above.

Figure 7A:
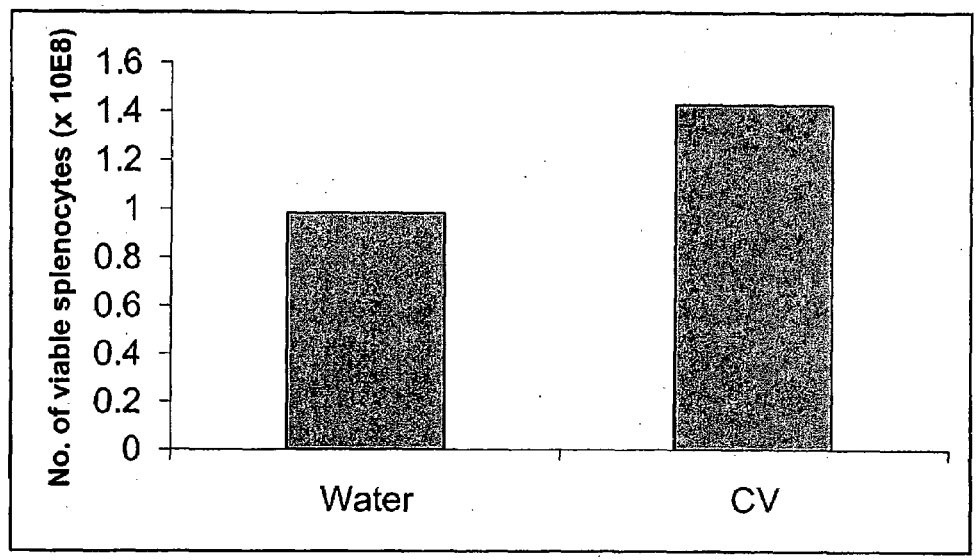
FIGS. 7A and 7B.

3. Effect of Oral Administration of CV Extract on the In Vivo Proliferation of Viable Murine Splenocytes from Normal Mice CV crude extract administered orally to mice (Group 3) increased the number of in vivo viable splenocytes by 40% when compared to control mice (Group 4). (See FIG. 7A.) Splenocytes were harvested and isolated as described in Example III, above. The resulting cell suspension was prepared, and the viability of the cell suspension was tested as described in Example III, above.

Figure 7B:
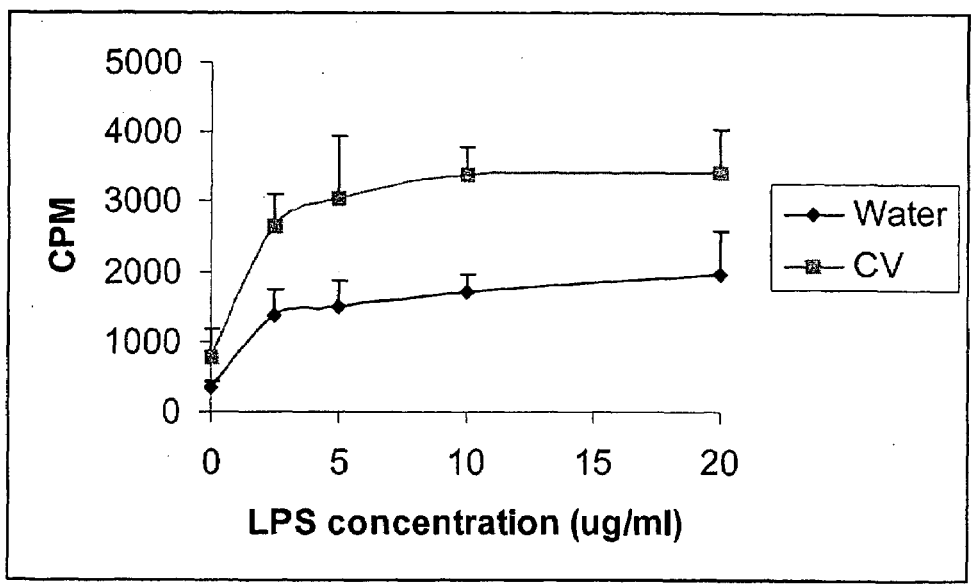

4. Effect of Oral Administration of CV Extract on the Ex Vivo Proliferation of LPS Stimulated Bone Marrow Cells from Normal Mice The bone marrow cells of mice treated with CV crude extract administered orally (Group 3) showed greater ex vivo LPS-stimulated proliferative activity than did the bone marrow cells of the control mice (Group 4). (See FIG. 7B.) The bone marrow cells were harvested and isolated as described in Example IV, above. The proliferative activity of CV crude extract on the bone marrow cells was tested as described in Example IV, above.

Example VII

Administration of CV Extract to Immunocompromised Mice or Severely Immunocompromised Mice Study Design Forty ICR mice were sorted into eight groups of 5 mice each. On day 1, the mice of Groups 1–4 were immunosuppressed by i.p. injection of 20 mg/kg cyclophosphamide. Also on day 1, the mice of Groups 5–8 were severely immunosuppressed by i.p. injection of 100 mg/kg cyclophosphamide. (See Table IV for the cyclophosphamide dose and dosing schedule.) On days 5, 6, and 7 following immunosuppression, Group 1 was treated with CV crude extract administered by i.p. injection; Group 2 was treated with normal saline administered i.p. On days 1–7 following immunosuppression, Group 3 was treated with CV crude extract administered orally; and, Group 4 was treated with deionized water. On days 1–7 following severe immunosuppression, Group 5 was treated with CV crude extract administered orally; and, Group 6 was treated with deionized water. On days 1–14 following severe immunosuppression, Group 7 was treated with CV crude extract administered orally; and, Group 8 was treated with deionized water. (See Table IV for the CV crude extract dose, dosing schedule, and route of administration.) Groups 2, 4, 6, and 8 are negative control groups. The mice of Groups 1–6 were sacrificed on day 8. The mice of Group 7 and Group 8 were sacrificed on day 15.

Groups 1–4 were injected with a cyclophosphamide solution prepared as follows. Cyclophosphamide 200 mg/vial (Endoxan-Asta) was purchased from Asta Medica. The cyclophosphamide was reconstituted as directed with sterile, deionized water. The concentration of the solution was adjusted to 1 mg/ml with sterile normal saline, aliquoted in sterile bottles, and stored at −80° C. The cyclophosphamide solution was prepared under aseptic conditions. On day 1, the cyclophosphamide solution was defrosted and injected into the mice of Groups 1–4.

Groups 5–8 were injected with a cyclophosphamide solution prepared as described for Groups 1–4 except that the concentration of the solution was adjusted to 5 mg/ml. On day 1, the cyclophosphamide solution was defrosted and injected into the mice of Groups 5–8.

The CV crude extract was prepared for i.p. or oral administration as described in Example VI, above.

TABLE IV

| Treatment Group | Number of Mice | Cyclophosphamide Dose & Dosing Schedule | CV Dose & Dosing Schedule | Route of Administration |
|---|---|---|---|---|
| 1 | 5 | 20 mg/kg/day on day 1 (0.5 ml of 1 mg/ml solution injected into an approximately 25 g mouse) | 50 mg/kg/day on days 5, 6, & 7 (0.25 ml of 5 mg/ml solution orally into an approximately 25 g mouse) | i.p injection |
| 2 | 5 | 20 mg/kg/day on day 1 (0.5 ml of 1 mg/ml solution injected into an approximately 25 g mouse) | 0.25 ml normal sterile saline pH 7.4 on days 5, 6, & 7 (0.25 ml of 5 mg/ml solution orally into an approximately 25 g mouse) | i.p injection |

TABLE IV-continued

| Treatment Group | Number of Mice | Cyclophosphamide Dose & Dosing Schedule | CV Dose & Dosing Schedule | Route of Administration |
|---|---|---|---|---|
| 3 | 5 | 20 mg/kg/day on day 1 (0.5 ml of 1 mg/ml solution injected into an approximately 25 g mouse) | 50 mg/kg/day on days 1–7 (0.25 ml of 5 mg/ml solution orally into an approximately 25 g mouse) | oral |
| 4 | 5 | 20 mg/kg/day on day 1 (0.5 ml of 1 mg/ml solution injected into an approximately 25 g mouse) | 0.25 ml deionized water on days 1–7 | oral |
| 5 | 5 | 100 mg/kg/day on day 1 (0.5 ml of 5 mg/ml solution injected into an approximately 25 g mouse) | 50 mg/kg/day on days 1–7 (0.25 ml of 5 mg/ml solution orally into an approximately 25 g mouse) | oral |
| 6 | 5 | 100 mg/kg/day on day 1 (0.5 ml of 5 mg/ml solution injected into an approximately 25 g mouse) | 0.25 ml deionized water on days 1–7 | oral |
| 7 | 5 | 100 mg/kg/day on day 1 (0.5 ml of 5 mg/ml solution injected into an approximately 25 g mouse) | 50 mg/kg/day on days 1–14 (0.25 ml of 5 mg/ml solution orally into an approximately 25 g mouse) | oral |
| 8 | 5 | 100 mg/kg/day on day 1 (0.5 ml of 5 mg/ml solution injected into an approximately 25 g mouse) | 0.25 ml deionized water on days 1–14 | oral |

Figure 8A:
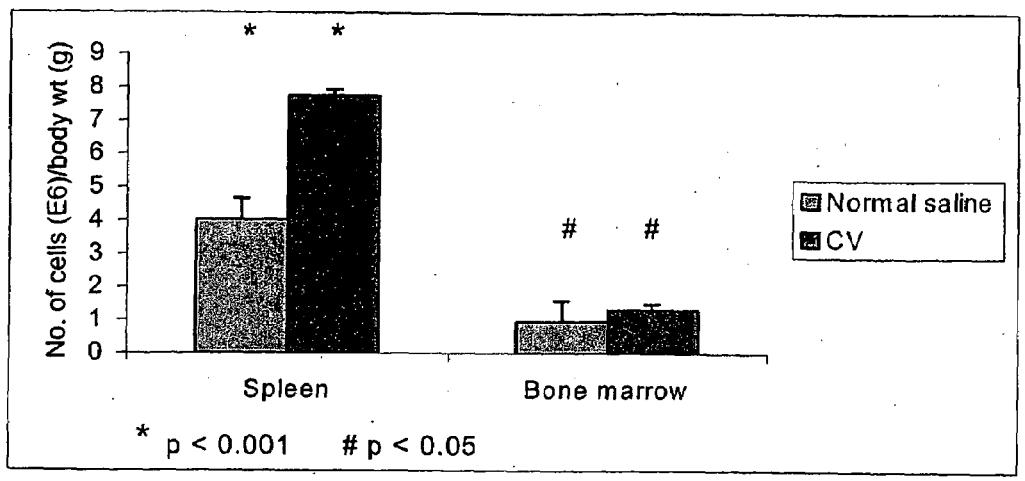
FIGS. 8A, 8B, and 8C.

1. Effect of i.p. Administration of CV Crude Extract on the In Vivo Proliferation of Viable Murine Splenocytes from Immunocompromised Mice CV crude extract administered i.p. to immunosuppressed mice (Group 1) significantly increased the number of in vivo viable splenocytes ($p<0.001$) as compared to the control mice (Group 2). (See FIG. 8A.) Splenocytes were harvested and isolated as described in Example III, above. The resulting cell suspension was prepared, and the viability of the cell suspension was tested as described in Example III, above.

2. Effect of i.p. Administration of CV Crude Extract on the In Vivo Proliferation of Viable Murine Bone Marrow Cells from Immunocompromised Mice The bone marrow cells of mice treated with CV crude extract administered i.p. (Group 1) significantly increased the number of in vivo viable bone marrow cells ($p<0.05$) than did the bone marrow cells of the control mice (Group 2). (See FIG. 8A) Bone marrow cells were harvested and isolated as described in Example IV, above. The viability of the bone marrow cells was tested as described in Example III, above.

Figure 8B:
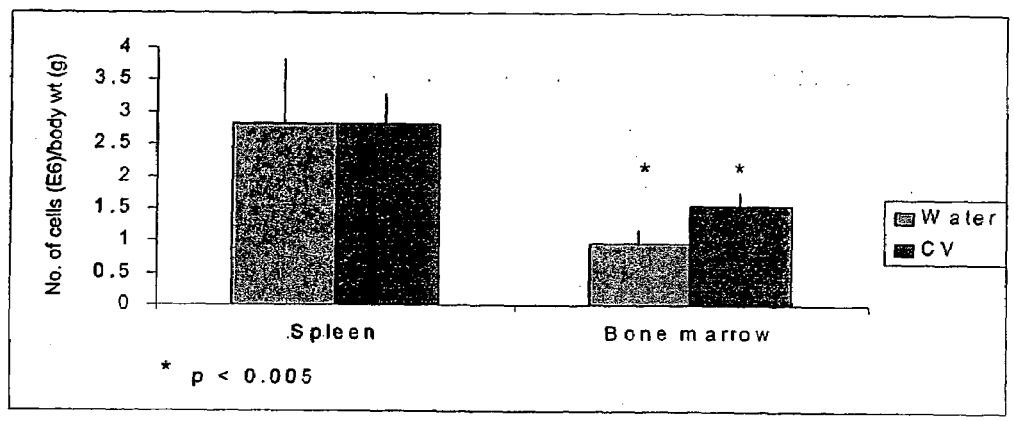

3. Effect of Oral Administration (Seven Day Dosing Schedule) of CV Extract on the In Vivo Proliferation of Viable Murine Splenocytes from Immunocompromised Mice CV crude extract administered orally to immunosuppressed mice (Group 3) did not increase the number of in vivo viable splenocytes as compared to the control mice (Group 4). (See FIG. 8B.) Splenocytes were harvested and isolated as described in Example III, above. The resulting cell suspension was prepared, and the viability of the cell suspension was tested as described in Example III, above.

4. Effect of Oral Administration (Seven Day Dosing Schedule) of CV Extract on the In Vivo Proliferation of Viable Murine Bone Marrow Cells from Immunocompromised Mice The bone marrow cells of mice treated with CV crude extract administered orally (Group 3) significantly increased the number of in vivo viable bone marrow cells ($p<0.005$) when compared to the bone marrow cells of the control mice (Group 4). (See FIG. 8B) The bone marrow cells were harvested and isolated as described in Example IV, above. The resulting cell suspension was prepared, and the viability of the cell suspension was tested as described in Example III, above.

Figure 8C:
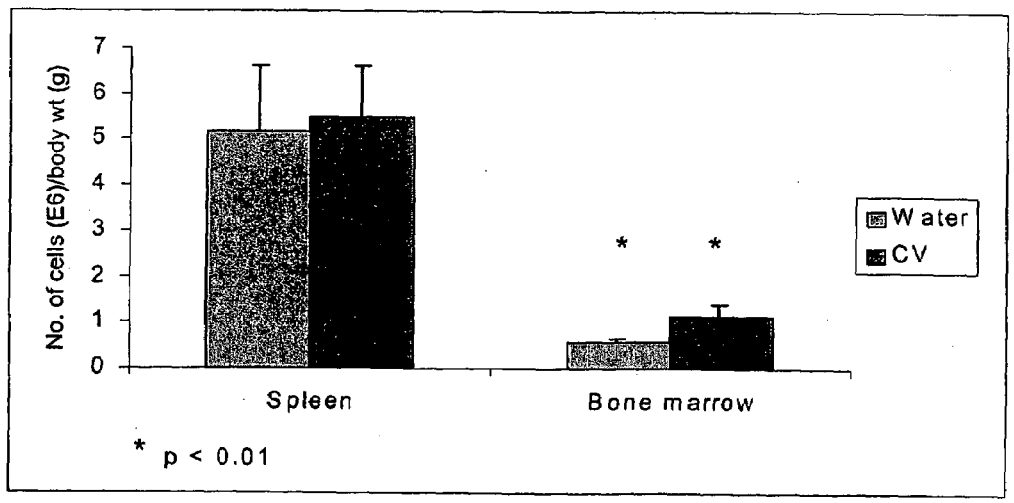

5. Effect of Oral Administration of CV Crude Extract (Seven Day Dosing Schedule) on the In Vivo Proliferation of Viable Murine Splenocytes from Severely Immunocompromised Mice CV crude extract administered orally to severely immunosuppressed mice (Group 5) increased the number of in vivo viable splenocytes as compared to the control mice (Group 6). However, the increase was not statistically significant. (See FIG. 8C.) Splenocytes were harvested and isolated as described in Example III, above. The resulting cell suspension was prepared, and the viability of the cell suspension was tested as described in Example III, above.

6. Effect of Oral Administration of CV Crude Extract (Seven Day Dosing Schedule) on the In Vivo Proliferation of Viable Murine Bone Marrow Cells from Severely Immunocompromised Mice CV crude extract administered orally to severely immunosuppressed mice (Group 5) significantly increased the number of in vivo viable bone marrow cells ($p<0.01$) as compared to the control mice (Group 6). (See FIG. 8C) Bone marrow cells were harvested and isolated as described in Example IV, above. The resulting cell suspension was prepared, and the viability of the cell suspension was tested as described in Example III, above.

Figure 9A:
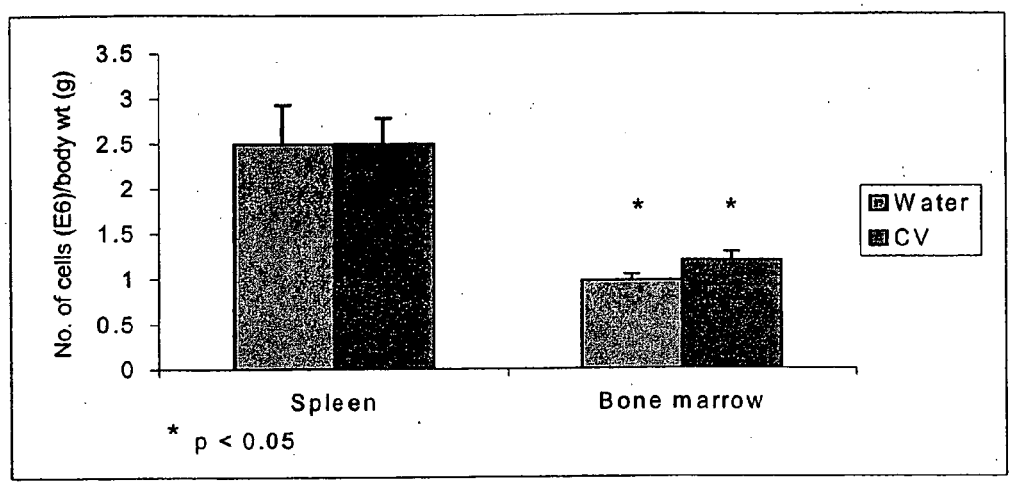
FIGS. 9A, 9B, and 9C.

7. Effect of Oral Administration (14 Day Dosing Schedule) of CV Crude Extract on the In Vivo Proliferation of Viable Murine Splenocytes from Severely Immunocompromised Mice CV crude extract administered orally to immunosuppressed mice (Group 7) did not increase the number of in vivo viable splenocytes when compared to the control mice (Group 8). (See FIG. 9A.) Splenocytes were harvested and isolated as described in Example III, above. The resulting cell suspension was prepared, and the viability of the cell suspension was tested as described in Example III, above.

8. Effect of Oral Administration (14 Day Dosing Schedule) of CV Extract on the In Vivo Proliferation of Viable Murine Bone Marrow Cells from Severely Immunocompromised Mice The bone marrow cells of mice treated with CV crude extract administered orally (Group 7) significantly increased the number of in vivo viable bone marrow cells ($p<0.05$) when compared to the control mice (Group 8). (See FIG. 9A.) Bone marrow cells were harvested and isolated as described in Example IV, above. The proliferative activity of CV crude extract on the bone marrow cells was tested as described in Example IV, above.

Figure 9B:
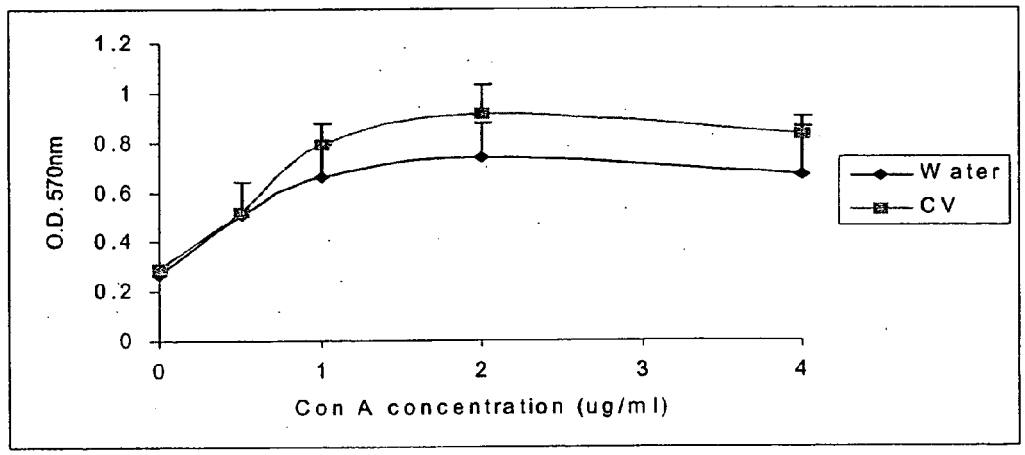

9. Effect of Oral Administration of CV Extract (14 Day Dosing Schedule) on the Ex Vivo Proliferation of Con A Stimulated Splenocytes from Severely Immunosuppressed Mice The splenocytes of mice treated with CV crude extract administered orally (Group 7) showed greater ex vivo proliferative activity than did the splenocytes of the control mice (Group 8). (See FIG. 9B.) The splenocytes were harvested and isolated as described in Example III, above. The proliferative activity of CV crude extract on the splenocytes was tested as described in Example III, above.

Figure 9C:
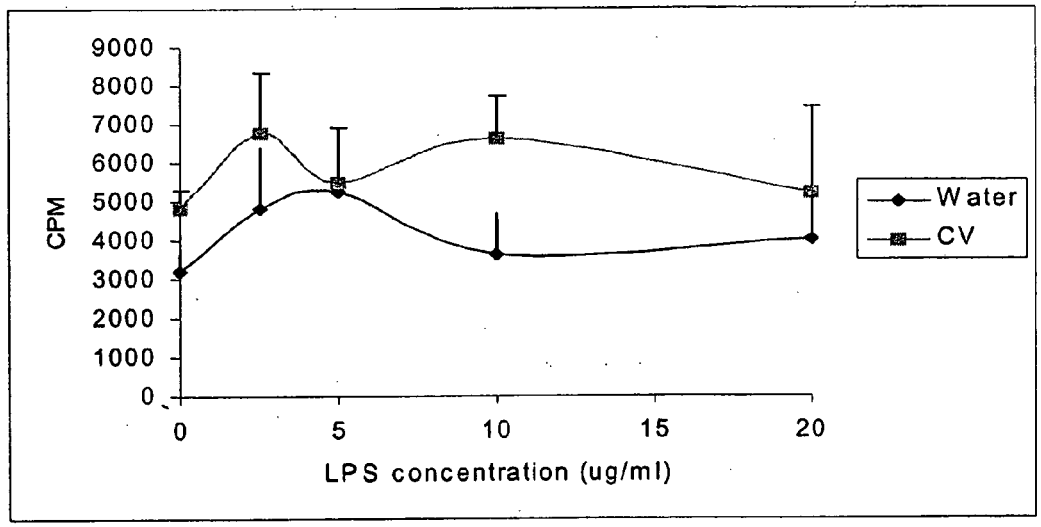

10. Effect of Oral Administration of CV Extract on the Ex Vivo Proliferation of LPS Stimulated Bone Marrow Cells from Severely Immunocompromised Mice The bone marrow cells of mice treated with CV crude extract administered orally (Group 7) showed greater ex vivo LPS-stimulated proliferative activity than did the bone marrow cells of the control mice (Group 8) ($p<0.05$). (See FIG. 9C.) The bone marrow cells were harvested and isolated as described in Example IV, above. The proliferative activity of CV crude extract on the bone marrow cells was tested as described in Example IV, above.

Example VIII

Dose Response Study in Immunocompromised Mice

Study Design

Twenty ICR mice were sorted into four groups of 5 mice each. On day 1, the mice of Groups 1–4 were immunosuppressed by i.p. injection of 20 mg/kg cyclophosphamide. (See Table V for the cyclophosphamide dose and dosing schedule.) On days 1–7, following cyclophosphamide administration, the mice of Groups, 1, 2, and 3 were treated with 5, 20, and 50 mg/kg/ day of CV crude extract administered orally. On days 1–7, following cyclophosphamide administration, the mice of Group 4 were treated with deionized water. (See Table V for the CV crude extract dose and dosing schedule.) Group 4 is a negative control group. The mice of Groups 1–4 were sacrificed on day 8.

The cyclophosphamide was prepared and administered as described in Example VII, above.

The CV crude extract for oral administration of 50 mg/kg/ day of CV crude extract was prepared as described in Example VI, above. The CV crude extract for oral administration of 5 mg/kg/day and 20 mg/kg/day CV crude extract was prepared as described in Example VI, above, except the concentrations of the solutions were adjusted to 0.5 mg/ml and 2 mg/ml, respectively.

TABLE V

| Treatment Group | Number of Mice | Cyclophosphamide Dose & Dosing Schedule | CV Dose & Dosing Schedule | Route of Administration |
|---|---|---|---|---|
| 1 | 5 | 20 mg/kg/day on day 1 (0.5 ml of 1 mg/ml solution injected into an approximately 25 g mouse) | 5 mg/kg/day on days 1–7 (0.25 ml of 0.5 mg/ml solution orally into an approximately 25 g mouse) | oral |
| 2 | 5 | 20 mg/kg/day on day 1 (0.5 ml of 1 mg/ml solution injected into an approximately 25 g mouse) | 20 mg/kg/day on days 1–7 (0.25 ml of 2 mg/ml solution orally into an approximately 25 g mouse) | oral |
| 3 | 5 | 20 mg/kg/day on day 1 (0.5 ml of 1 mg/ml solution injected into an approximately 25 g mouse) | 50 mg/kg/day on days 1–7 (0.25 ml of 5 mg/ml solution orally into an approximately 25 g mouse) | oral |
| 4 | 5 | 20 mg/kg/day on day 1 (0.5 ml of 1 mg/ml solution injected into an approximately 25 g mouse) | 0.25 ml deionized water on days 1–7 | oral |

Figure 10:
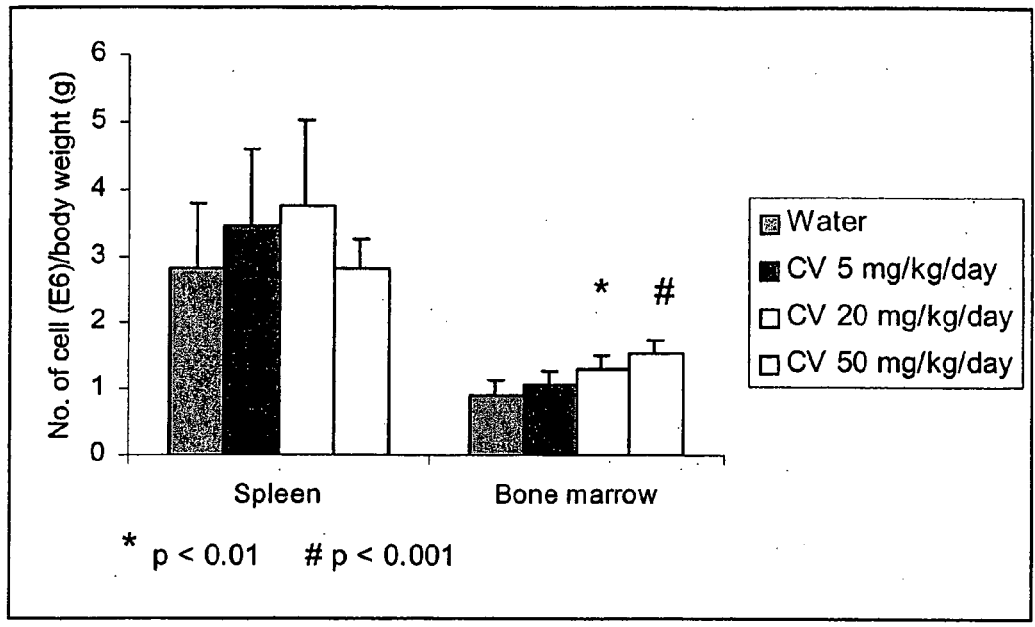
FIG. 10 illustrates the in vivo effect on viable splenocytes and bone marrow cells of immunocompromised mice treated with various dosages of CV crude extract administered orally (7 day dosing schedule).

1. Effect of Oral Administration of Different Dosages of CV Extract on the In Vivo Proliferation of Viable Murine Splenocytes from Immunosuppressed Mice CV crude extract administered orally to mice at 5 mg/kg/day (Group 1) and at 20 mg/kg/day (Group 2) increased the number of in vivo viable splenocytes in a dose dependent manner when compared to the control mice (Group 4). (See FIG. 10.) CV crude extract administered orally to mice at 50 mg/kg/day (Group 3) did not increase the number of in vivo viable splenocytes when compared to control mice (Group 4). (See FIG. 10.) The data presented for the Group 3 mice is consistent with the result presented in Example VIII and FIG. 8A, discussed above.

Splenocytes were harvested and isolated as described in Example III, above. The resulting cell suspension was prepared, and the viability of the cell suspension was tested as described in Example III, above.

2. Effect of Oral Administration of Different Dosages of CV Extract on the In Vivo Proliferation of Viable Murine Bone Marrow Cells from Immunosuppressed Mice CV crude extract administered orally to mice at 5 mg/kg/day (Group 1), at 20 mg/kg/day (Group 2), and 50 mg/kg/day (Group 3) increased the number of in vivo viable bone marrow cells in a dose dependent manner when compared to the control mice (Group 4). (See FIG. 10.) CV extract administered orally to the mice of Group 2 increased the proliferation of bone marrow cells ($p<0.01$) as compared to the control mice (Group 4); and, CV extract administered orally to the mice of Group 3 increased the proliferation of bone marrow cells ($p<0.001$) as compared to the control mice (Group 4).

The bone marrow cells were harvested and isolated as described in Example IV, above. The resulting cell suspension was prepared, and the viability of the cell suspension was tested as described in Example III, above.

Example IX

Oral Administration of CV Extract to Normal Mice, Immunocompromised Mice, and Severely Immunocompromised Mice: Effect on Cell-mediated Immune Response Study Design A mouse model is used to determine increases in cell-mediated immune responses. Contact hypersensitivity is a cell-mediated immune response. This model is based on standard contact hypersensitivity studies, which rely on mouse ear swelling measurement to determine the expression of contact hypersensitivity.

Thirty-six mice were then sorted into six groups of 6 mice each. To allow for future identification of individuals, each mouse was marked on its tail. Groups 1 and 2 were normal mice; Groups 3 and 4 were immunocompromised mice; and, Groups 5 and 6 were severely immunocompromised mice. On days 1–7, Groups 1, 3, and 5 were treated with 50 mg/kg/day of CV crude extract administered orally. On days 1–7 Groups 2, 4, and 6 were treated with 0.25 ml of deionized water administered orally. On days 3 and 4, all thirty-six mice were sensitized with 2,4-dinitro-1-fluorobenzene (DNFB). On day 7, all thirty-six mice were challenged with DNFB. On day 8, ear measurements were taken of all thirty-six mice. (See Table VI.)

The CV crude extract was prepared for oral administration to Groups 1, 3, and 5 as described in Example VI, above. The CV crude extract was administered as described in Example VI and Table III, above. (Also see Table VI for the CV crude extract dose and dosing schedule.)

The cyclophosphamide was prepared for storage and administration as discussed in Example VII, above. The mice of Groups 3 and 4 were immunosuppressed by administration of 20 mg/kg on day 1 as described in Example VII and Table IV, above. The mice of Groups 5 and 6 were severely immunosuppressed by administration of 100 mg/kg on day 1 as described in Example VII and Table IV, above. (Also see Table VI for the cyclophosphamide dose and dosing schedule.)

On days 3 and 4, all thirty-six mice were sensitized with 2,4-dinitro-1-fluorobenzene (DNFB) as follows. Exposures are accomplished by the direct application of 25 µl of 0.25% w/v DNFB to the shaved abdomen of each mouse with a pipette, and by the direct application of 5 µl of 0.25% w/v DNFB to each footpad of each mouse. On day 7, all thirty-six mice were challenged with 2,4-dinitro-1-fluorobenzene (DNFB) as follows. Exposures are accomplished by the direct application of 10 µl of 0.20% w/v DNFB to both sides of each ear of each mouse with a pipette. On day 8, ear measurements of the ear thickness were made using a digital caliper, i.e., Mitutoyo digital micrometer.

TABLE VI

| Treatment Group | No. of Mice | Cyclophosphoamide Dose (administered i.p.) & Dosing Schedule | DNFB Dose & Dosing Schedule | CV Dose (administered orally) & Dosing Schedule |
|---|---|---|---|---|
| 1 | 6 | N/A | 25 µl 0.25% w/v DNFB painted on the shaven abdomen and 5 µl on each footpad on days 3 & 4. 10 µl 0.2% w/v DNFB painted on both sides of each ear of day 7 Ear thickness measured on day 8 | 50 mg/kg/day on days 1–7 (0.25 ml) (0.25 ml of 5 mg/ml solution orally into an approximately 25 g mouse) |
| 2 | 6 | N/A | Same as Group 1 | 0.25 ml deionized water on days 1–7 |
| 3 | 6 | 20 mg/kg/day on day 1 (0.5 ml of 1 mg/ml solution injected into an approximately 25 g mouse) | Same as Group 1 | 50 mg/kg/day on days 1–7 (0.25 ml of 5 mg/ml solution orally into an approximately 25 g mouse) |
| 4 | 6 | 20 mg/kg/day on day 1 (0.5 ml of 1 mg/ml solution injected into an approximately 25 g mouse) | Same as Group 1 | 0.25 ml deionized water on days 1–7 |
| 5 | 6 | 100 mg/kg/day on day 1 (0.5 ml of 5 mg/ml solution injected into an approximately 25 g mouse) | Same as Group 1 | 50 mg/kg/day on days 1–7 (0.25 ml of 5 mg/ml solution orally into an approximately 25 g mouse) |
| 6 | 6 | 100 mg/kg/day on day 1 (0.5 ml of 5 mg/ml solution injected into an approximately 25 g mouse) | Same as Group 1 | 0.25 ml deionized water on days 1–7 |

1. Results in Normal Mice Orally Treated with CV Extract

Figure 11:
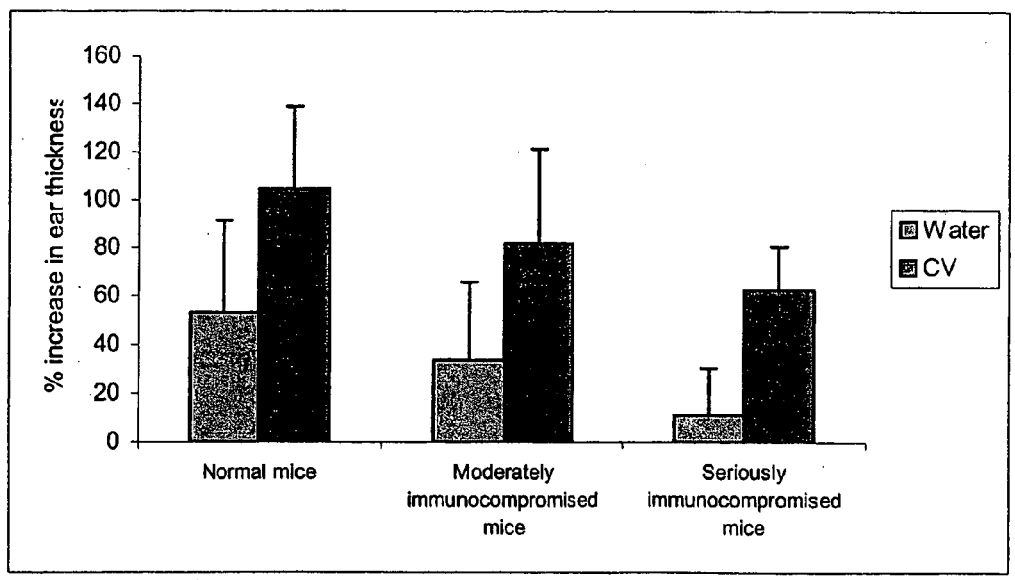
FIG. 11 illustrates ear measurements of normal, immunosuppressed, and severely immunosuppressed mice treated with CV crude extract administered orally, and then challenged with 2,4-dinitro-1-fluorobenzene (DNFB).

Normal mice (Group 1) showed a significantly greater hypersensitivity response ($p<0.05$), as measured by mouse ear swelling, than did the control mice (Group 2). (See FIG. 11.)

2. Results in Immunosuppressed Mice Orally Treated with CV Extract

Immunosuppressed mice (Group 3) showed a significantly greater hypersensitivity response ($p<0.05$), as measured by mouse ear swelling, than did the control mice (Group 4). (See FIG. 11.)

The hypersensitivity response of the immunosuppressed mice (Group 3) was not significantly different from the hypersensitivity response in control mice (Group 2).

3. Results in Severely Immunosuppressed Mice Orally Treated with CV Extract

Severely immunosuppressed mice (Group 5) showed a significantly greater hypersensitivity response ($p<0.001$), as measured by mouse ear swelling, than did the control mice (Group 6). (See FIG. 11.)

The hypersensitivity response ($p<0.001$) of the severely immunosuppressed mice (Group 5) was greater than the hypersensitivity response (p<0.05) observed in the immunosuppressed mice (Group 3) or in the normal mice (Group 1) (p<0.05).

Example X

Long Term (30 Days) Oral Administration of CV Extract to Normal Mice

Study Design

Ten ICR mice were sorted into two groups of 5 mice each. As shown in Table VII, Group 1 was treated with CV crude extract administered orally and, Group 2 was treated with deionized water administered orally, as a negative control. Table VII shows the dose and dosing schedule of each group. The mice of both groups were sacrificed on day 31. The CV crude extract was prepared, stored, and administered as discussed in Example VI, above. (Also, see Table VII.)

TABLE VII

| Treatment Group | Number of Mice | CV Dose | CV Dosing Schedule | Route of Administration |
|---|---|---|---|---|
| 1 | 5 | 50 mg/kg/day (0.25 ml of 5 mg/ml solution orally into an approximately 25 g mouse) | On days 1–30 | oral |
| 2 | 5 | 0.25 ml deionized water | On days 1–30 | oral |

Figure 12A:
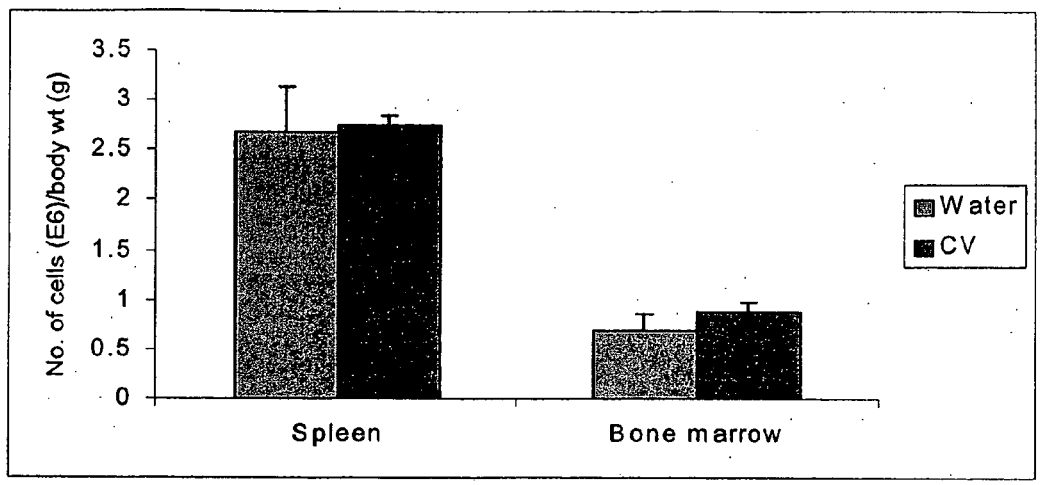
FIGS. 12A, 12B and 12C.

1. Effect of Long-term Oral Administration (30 Days) of CV Crude Extract on the In Vivo Proliferation of Viable Murine Splenocytes from Normal Mice CV crude extract administered orally to mice (Group 1) did not significantly increase the number of in vivo viable splenocytes when compared to control mice (Group 2). (See FIG. 12A.) Splenocytes were harvested and isolated as described in Example III, above. The resulting cell suspension was prepared, and the viability of the cell suspension was tested as described in Example III, above.

2. Effect of Long-term Oral Administration of CV Crude Extract on the In Vivo Proliferation of LPS Stimulated Murine Bone Marrow Cells from Normal Mice CV crude extract administered orally to mice (Group 1) did not significantly increase the number of in vivo viable bone marrow cells when compared to control mice (Group 2). (See FIG. 12A.) The bone marrow cells were harvested and isolated as described in Example IV, above. The viability of the bone marrow cells was tested as described in Example III, above.

Figure 12B:
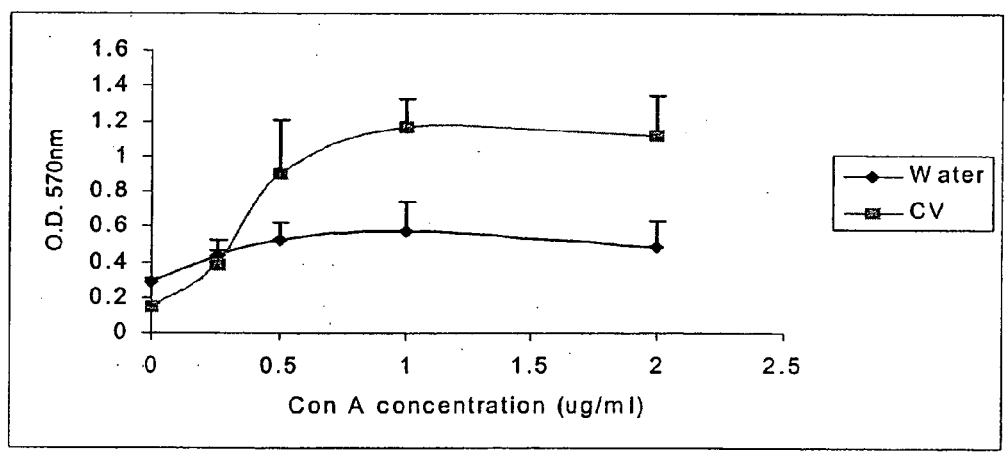

3. Effect of Long-term Oral Administration of CV Extract on the Ex Vivo Proliferation of Viable Murine Splenocytes from Normal Mice The proliferative response of splenocytes treated with CV crude extract (Group 1) was greater than the proliferative response of the control mice (Group 2). (See FIG. 12B.) Splenocytes were harvested and isolated as described in Example III, above. The resulting cell suspension was prepared, and the viability of the cell suspension was tested as described in Example III, above. The splenocytes were stimulated with Con A, and the stimulation index was calculated as discussed in Example V, above.

Figure 12C:
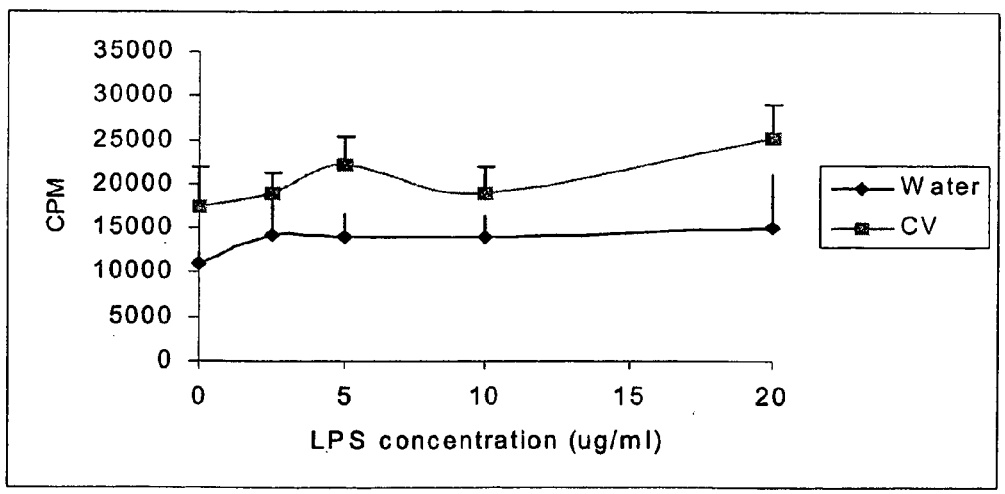

4. Effect of Long-term Oral Administration of CV Extract on the Ex Vivo Proliferation of LPS Stimulated Bone Marrow Cells from Normal Mice The bone marrow cells of mice treated with CV crude extract administered orally (Group 1) showed greater ex vivo LPS-stimulated proliferative activity than did the bone marrow cells of the control mice (Group 2). (See FIG. 12C)

The bone marrow cells were harvested and isolated as described in Example IV, above. The proliferative activity of CV crude extract on the bone marrow cells was tested as described in Example IV, above.

Example XI

Acute Toxicity of Orally Administered CV Crude Extract

On day 1, five ICR mice of each gender were treated with 1 g/kg CV crude extract administered orally, and observed for toxic signs for up to 14 days. No mice died during the observation period, and none of the ten mice showed any toxic sign over the entire observation period.

The CV crude extract was prepared for oral administration (except the concentration) to the ten mice as described in Example VI, above. The CV crude extract was administered once.

The CV crude extract administered to the ten mice was free of endotoxin contamination. A 2 mg/ml sample of the CV crude extract was subjected to an endotoxin test. The test was performed using a Limulus Amebocyte Lysate (LAL) test kit (Cape Cod Ltd. having a detection limit of 0.25 EU/ml LAL.

Example XII

Figure 13:
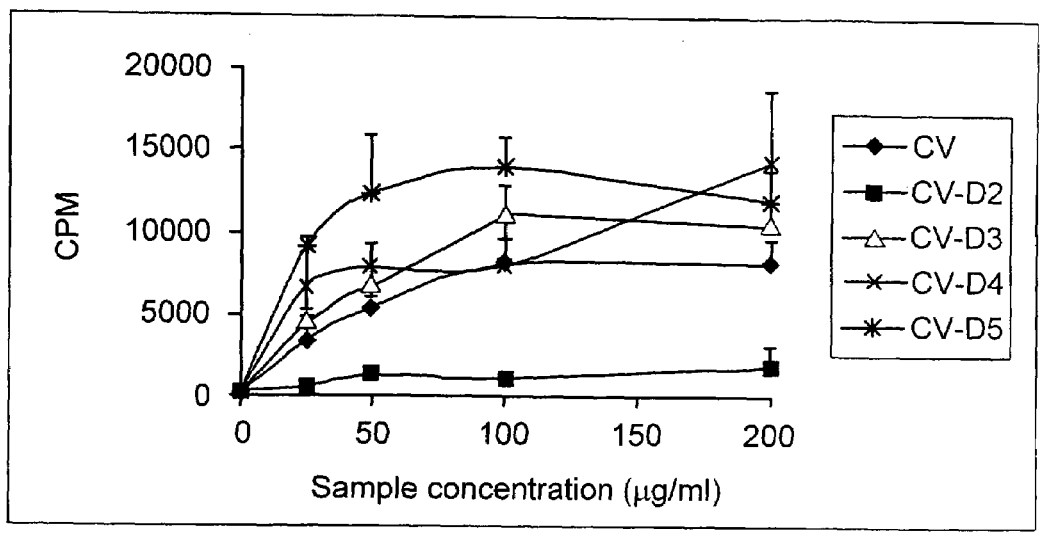
FIG. 13 illustrates the proliferation of viable murine splenocytes contacted with crude CV extract, CV-D2, CV-D3, CV-D4, and CV-D5 in vitro.

Effect of Negative Charge Density on the Immunological Activity of Peptide-linked Glucan The in vitro immunological activities of CV-peptide-linked glucans fractionated into various negative charge density groups by means of anion exchange chromatography, i.e., C1D2, C1D3, C1D4, and C1D5, were compared. FIG. 13 illustrates the proliferation of viable murine splenocytes contacted with C1D2, C1D3, C1D4, and C1D5 in vitro. A large difference in immunological potency was observed among the various fractions. Peptide-linked glucans of high negative charge density displayed a higher maximal activity (i.e., plateau level) and potency (i.e., steeper rise of activity at low sample concentration) than those of low-negative-charge-density fraction and the unfractionated CV extract. This indicates that negative charge density is an important determinant of the immunogenicity of the CV-derived peptide-linked glucans. In vitro immunological activity was assessed as described in Example III, above.

Example XIII

Figure 14:
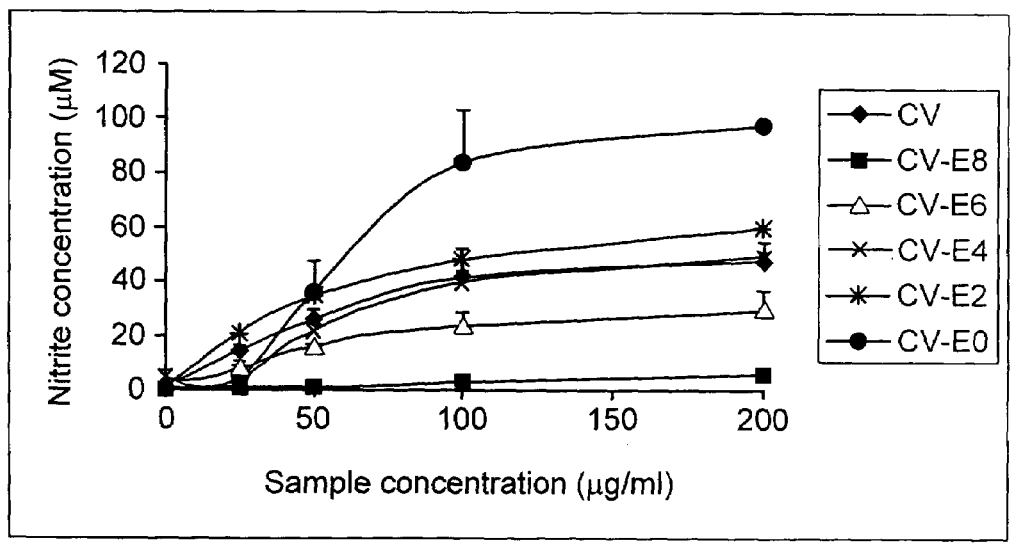
FIG. 14 illustrates the increased secretion of nitric oxide by murine peritoneal macrophages contacted with CV crude extract, CV-E8, CV-E6, CV-E4, CV-E2, and CV-E0 in vitro.

Effect of Molecular Weight on the Immunological Activities of Peptide-linked Glucans The in vitro immunological activity was determined for fractions C1E8, C1E6, C1E4, C1E2, and C1E0. FIG. 14 illustrates the increased secretion of nitric oxide by murine peritoneal macrophages contacted with C1E8, C1E6, C1E4, C1E2, and C1E0 in vitro. The immunological activity was not confined to a particular molecular weight range. C1E8, C1E6, C1E4, C1E2, and C1E0 afforded a similar dose-response profile, reaching a plateau between 100 and 200 μg/ml. The maximum (plateau) activities increased with increasing molecular weight of the fraction. In vitro immunological activity was assessed as described in Example III, above.

Example XIV

Preparation of Coriolus versicolor Partially Purified Extract

The Coriolus versicolor (CV) partially purified extract was prepared by dissolving CV crude extract as prepared by the method described in Example I, performing two chromatographic separation steps, and an ethanolic fractionation step. The CV crude extract solution was subjected to a first chromatographic step, e.g., a CM cellulose column, to remove cationic substances. The resulting effluent was subjected to a second chromatographic, e.g., a DEAE cellulose column, step to bind anionic substances. This effluent was then subjected to a separation protocol based on molecular weight, e.g. ethanolic fractionation or gel filtration. The resulting effluent, CV partially purified extract, may be further purified by any purification technique that further removes cations from the CV partially purified extract.

FIG. 15 is a flow chart illustrating the steps used in a protocol for further purification of the active components in the crude CV extract of FIG. 1. 1.0 g of CV crude extract, as prepared by the method of Example I, was dissolved in deionized water. The dissolved CV crude extract was centrifuged at 4000 rpm for 10 minutes to remove insoluble substances. Next, the supernatant was filtered through 0.45 μm filter (IWAKI) to further remove insoluble particles.

A Fibrous (Sigma) CM cellulose 600 ml open glass column (Bio-Rad) was equilibrated by washing the resin 3 times with 0.5 M NaOH for 30 minutes each time, and then 3 times with 0.5 M HCl for 30 minutes each time. The column was equilibrated with deionized water.

The supernatant was then run over the column and the effluent collected. (See FIG. 15 for buffer conditions.) The fractions were assayed for activity. Fraction C1 displayed activity, was run over a DEAE cellulose column, and the effluent collected. (See FIG. 15 for buffer conditions.) The fractions were assayed for activity. Fraction C1D5 was subjected to ethanolic fractionation (see FIG. 15 for buffer conditions.), and the resulting fractions were assayed for activity using murine splenocytes, as described in Example III. Fractions C1D5E8, C1D5E7, C1D5E4, and C1D5EX, CV partially purified extract displayed activity. Fractions C1D5E8, C1D5E7, C1D5E4, and C1D5EX were lyophilized, and weighed 5, 14, 49, and 13 mg, respectively. Further purification steps, especially those which remove cationic molecules may be performed on fractions C1D5E8, C1D5E7, C1D5E4, and C1D5EX.

Example XV

Figure 16:
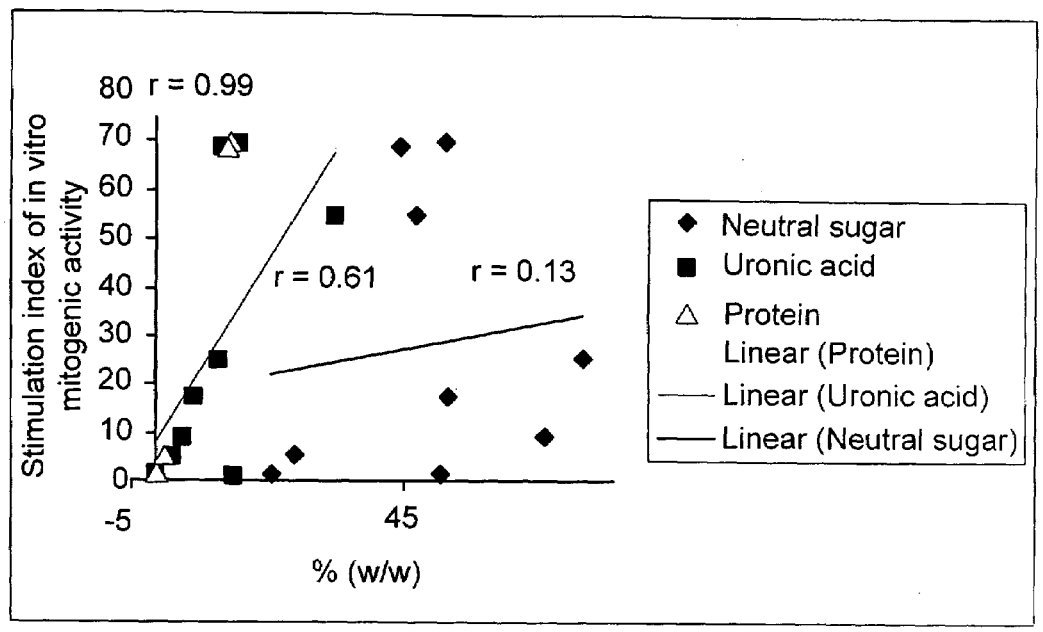
FIG. 16 illustrates the correlation of the composition of the CV fraction basic structural units (neutral sugar, uronic acid and protein/peptide) with in vitro mitogenic activities.

Role of the Peptide Moiety as an Antigenic Determinant in the CV Peptide-linked Glucans This example correlates the composition of the CV fraction basic structural units (neutral sugar, uronic acid and protein/peptide) with in vitro mitogenic activities. FIG. 16 shows the correlation between the stimulation index of the in vitro mitogenic response and the content of the basic structural units of the respective fractions. For the CV fractions analyzed, the peptide contents were strongly correlated ($r=0.99$, $p<0.05$) with the mitogenic activity. The correlation coefficient between the mitogenic activity and the uronic acid content was barely significant at the 10% level ($r=0.61$), and the correlation with the neutral sugar was insignificant. In vitro immunological activity was assessed as described in Example III, above.

Example XVI

Physicochemical and Biological Characterization of the CV Partially Purified Fractions The molecular weight range and average molecular weight was determined for fractions C1D5E8, C1D5E7, and C1D5EX. (See Table A.)

TABLE A

| Molecular weight range of C1D5E8, C1D5E7 and C1D5EX | |
|---|---|
| Fraction | Original (kDa) |
| C1D5E8 | 0.7–2.6; mean = 0.8 |
| C1D5E7 | 1.6–52; mean = 2.6 |
| C1D5EX | 0.8–111 (serious tailing of the peak); mean = 6.2 |

The content of neutral sugars, uronic acid and protein was determined for fractions C1D5E8, C1D5E7, and C1D5EX. (see Table B)

TABLE B

| Chemical composition of C1D5E8, C1D5E7 and C1D5EX: | | | |
|---|---|---|---|
| Fraction | Carbohydrate content (% by total mass) | Uronic acid content (% by total mass) | Protein content (% by total mass) |
| C1D5E8 | 18.77 ± 1.20 | 1.32 ± 0.15 | 5.04 ± 0.21 |
| C1D5E7 | 33.72 ± 1.48 | 5.23 ± 4.28 | 12.01 ± 0.24 |
| C1D5EX | 75.86 ± 6.82 | 16.95 ± 0.92 | 8.76 ± 0.31 |

The content of neutral sugars, uronic acid and protein was determined for fractions C1D5E8, C1D5E7, and C1D5EX as described in Example II. Based on the GC/MS analysis, glucose was the only detectable monosugar. Glucose molecules were connected by a $1 \rightarrow 3$ linkage.

The amino acid sequence of the protein/peptide moiety of the fraction C1D5E7 was determined to be Asp-Cys-Pro-Pro-Cys-Glu (SEQ ID NO:1). SEQ ID NO:1 was determined using an amino acid sequencer (Hewlett Packard 1000A protein sequencer equipped with an HPLC system).

Figure 17:
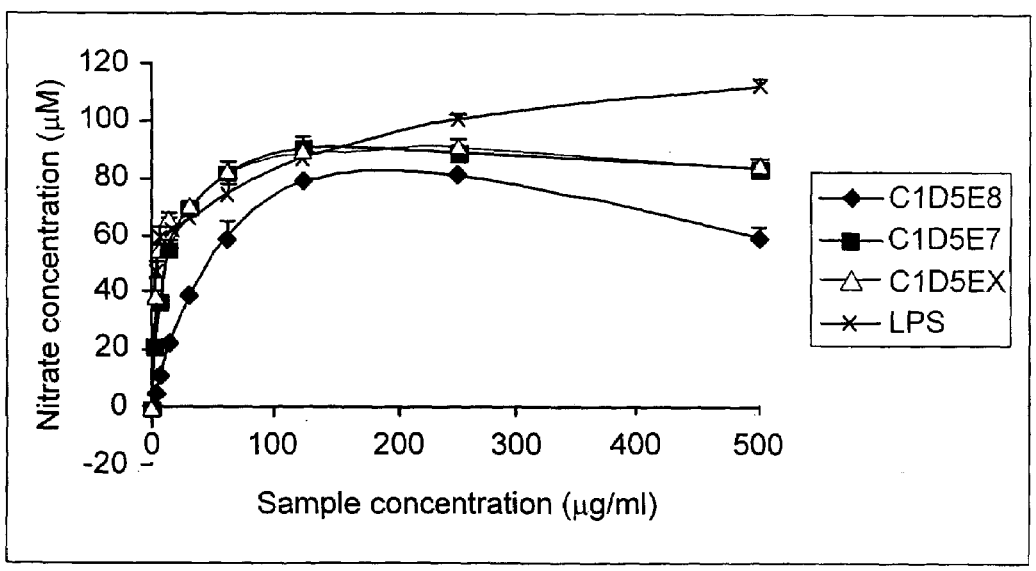
FIG. 17 shows the in vitro stimulatory activities of three active partially purified CV fractions, namely, C1D5E8, C1D5E7 and C1D5EX, on the secretion of nitric oxide by murine peritoneal macrophages.

The immunological activities of CV partially purified fractions C1D5E8, C1D5E7 and C1D5EX (see FIG. 15) were determined. FIG. 17 shows the in vitro stimulatory activities of three active partially purified CV fractions, namely C1D5E8, C1D5E7 and C1D5EX, on the secretion of nitric oxide by murine peritoneal macrophages. All the CV partially purified fractions were found to be as active and potent as LPS. (See FIG. 17.)

Example XVII

Effect of the Molecular Weight of CV Crude Extract and of CV Partially Purified Extract on Intestinal Permeability The intestinal permeability of CV crude extract and CV partially purified extract, fractions C1D5E8, C1D5E7 and C1D5EX, were determined in vitro using the Caco-2 cell monolayer Transwell method. The molecular weight distributions of the native CV samples and their Caco-2 cell-permeable compounds were compared. The analyses were performed using an HPLC system coupled with a Superdex 75 10/30 column. The elution buffer was 200 mM sodium chloride solution pH 7.0, and the eluants were monitored at UV 210 nm.

All experiments were carried out under temperature-controlled conditions at 37° C. Phosphate buffer saline (PBS) incorporated with 80 mM magnesium chloride and 90 mM calcium chloride was used as the transport buffer for all permeability measurements. Before the experiment, the cell monolayer was washed with the transport buffer twice. 1.5 ml transport buffer containing the samples to be tested was added to the basolateral side of the Caco-2 cell monolayer. After equilibration at 37° C. for 30 min, the Transwell together with the sample solution was transferred to a cluster plate previously filled with 2.6 ml transport buffer. The components that permeated through the cells were collected at the basolateral side at the end of the experiment. The collected samples were desalted and lyophilized for subsequent chemical and biological characterization.

1. CV Crude Extract

The components of CV crude extract-permeable to Caco-2 cell monolayer (kDa) are shown in Table C, below.

Figure 18A:
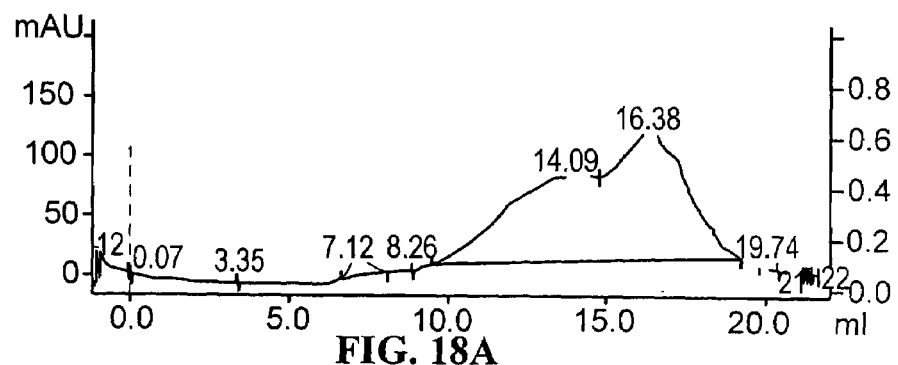
FIGS. 18A and 18B.
Figure 18B:
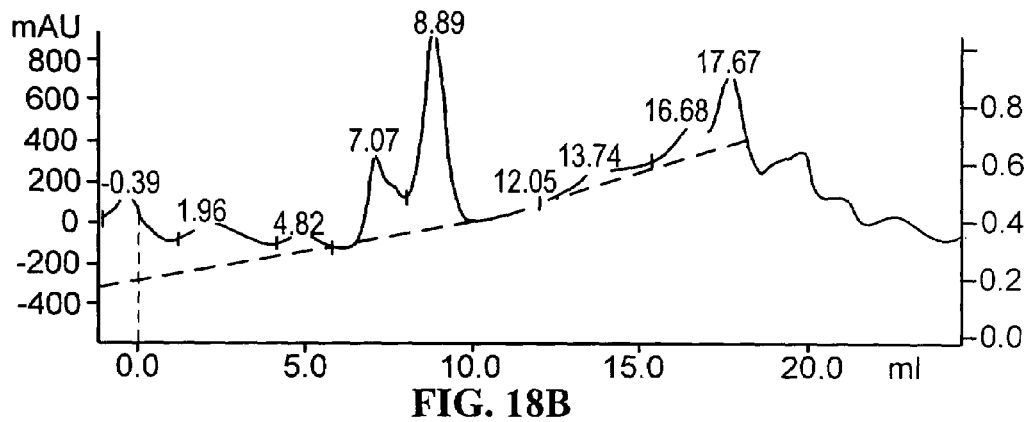

FIG. 18A is a size exclusion chromatogram of CV crude extract, and FIG. 18B illustrates CV crude extract Caco-2 cell-permeable contents collected after the transport study. The CV crude extract as prepared in Example I ranged from 0.5–40 kDa, averaging 2.6 kDa. As illustrated by FIG. 18B, the peaks eluted at 7.07 and 8.89 ml were present in every sample collected in the basolateral chamber (including the control, i.e., no CV crude extract). This result suggests the peaks are not indigenous to the CV crude extract samples, but are possibly due to macromolecules being eroded from the Caco-2 cells. The peak eluted in 17.67 ml fraction is likely due to the small molecules rather than the bioactive glucans present in the CV crude extract. Based on the molecular weight profiles shown in FIGS. 18A and 18B, we conclude that the low-molecular-weight constituents traverse across the monolayer more readily than their high-molecular-weight counterparts. Additionally, we conclude that 3 kDa is possibly the upper molecular weight limit for the intestinal absorption of the CV crude extract.

TABLE C

Molecular weight range of C1D5E8, C1D5E7 and C1D5EX

| | Components permeable to Caco-2 cell monolayer (kDa) |
|---|---|
| CV crude extract | 0.3–5 (but mainly between 0.3–3) mean = 0.7 |

2. CV Partially Purified Extract: C1D5E8, C1D5E7 and C1D5EX

The components of fractions C1D5E8, C1D5E7 and C1D5E permeable to Caco-2 cell monolayer (kDa) are shown in Table D, below.

Figure 19A:
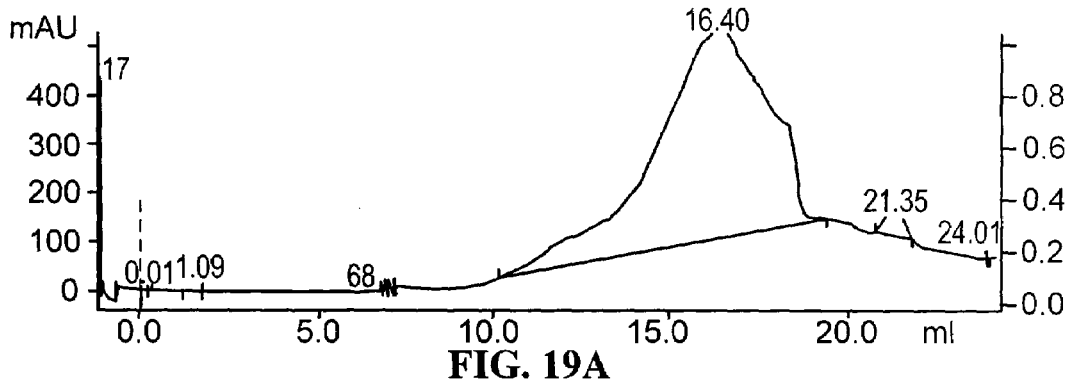
FIGS. 19A and 19B.
Figure 19B:
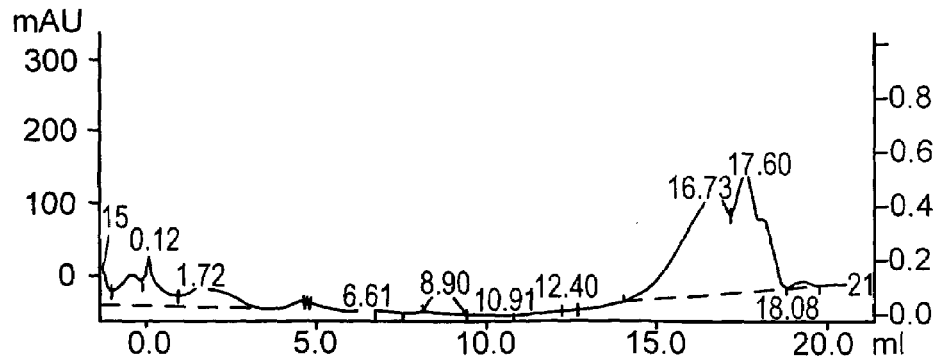

FIG. 19A is a size exclusion chromatogram of the Caco-2 cell-permeable substances in C1D5E8. The average molecular weight of C1D5E8 was 0.8 kDa. As shown in FIG. 19B, a substantial amount of peptide-linked glucan was eluted in 16.73 ml, indicating that the constituents of about 0.7 kDa present in C1D5E8 were transported across the monolayer in the in vitro absorption model.

Figure 20A:
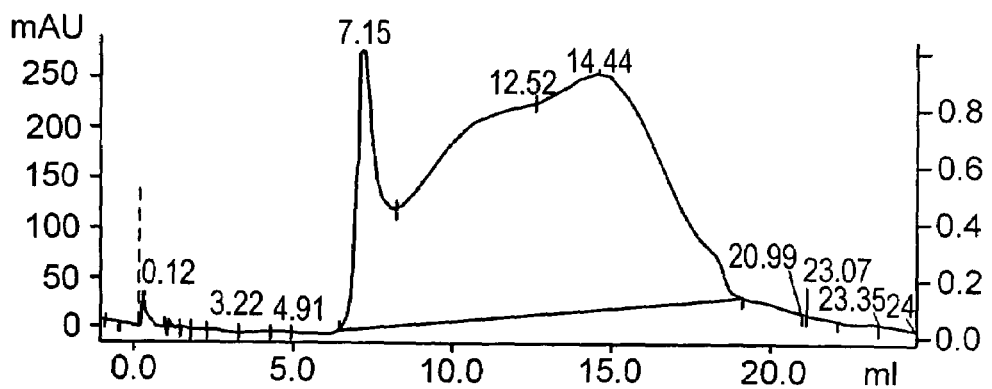
FIGS. 20A and 20B.
Figure 20B:
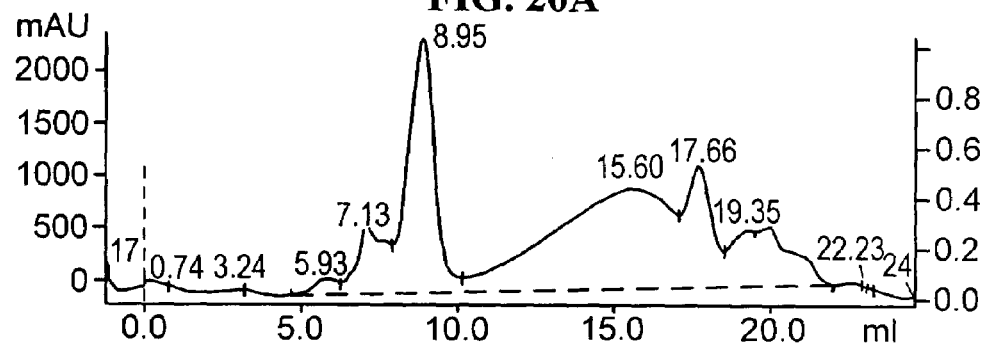

FIG. 20A is a size exclusion chromatogram of the Caco-2 cell-permeable substances in C1D5E7. C1D5E7 had an average molecular weight of 2.6 kDa. (See FIG. 20A.) At the end of the transport study, only the lower molecular weight components (i.e., mean molecular weight of 1.2 kDa) could be detected in the basolateral side of the Caco-2 cell monolayer. (See FIG. 20B.)

Figure 21A:
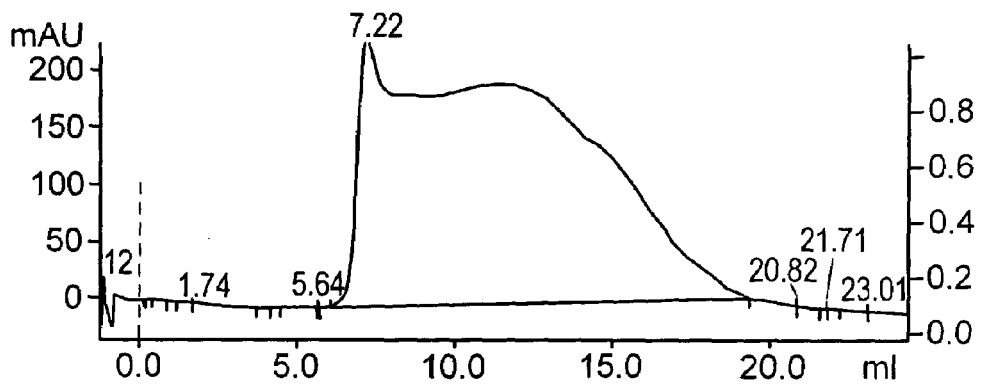
FIGS. 21A and 21B.
Figure 21B:
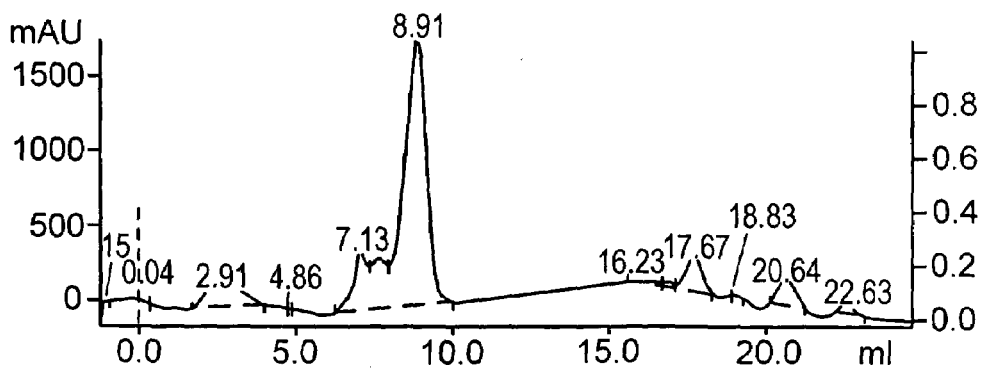

FIG. 21A is a size exclusion chromatogram of the Caco-2 cell-permeable substances in C1D5EX. The average molecular weight of C1D5EX was estimated to be about 6 kDa. (See FIG. 21A.) FIG. 21B shows that apart from the small molecules eluted at 17.67 ml, a very small amount of other components also permeated through the intestinal barrier to the basolateral side of the monolayer.

TABLE D

Molecular weight range of C1D5E8, C1D5E7 and C1D5EX

| Fractions | Components permeable to Caco-2 cell monolayer (kDa) |
|---|---|
| C1D5E8 | 0.3–2 mean = 0.7 |
| C1D5E7 | 0.3–5 (but mainly between 0.3–3); mean = 1.2 |
| C1D5EX | insignificant amount detected |

Example XVIII

Figure 22:
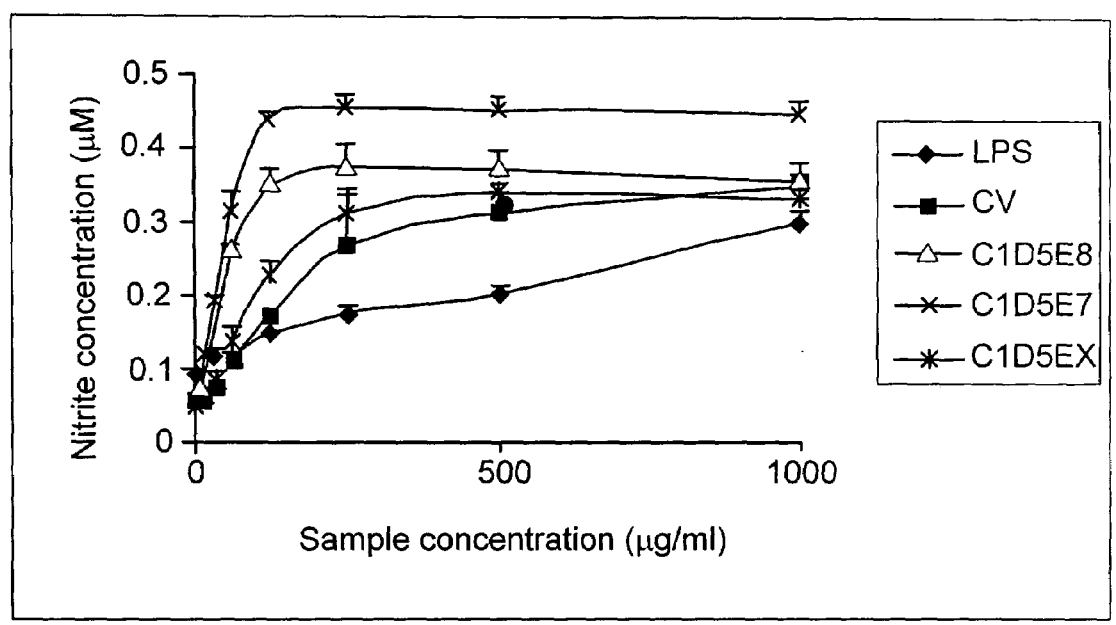
FIG. 22 illustrates the in vitro effect on the secretion of nitric oxide by murine peritoneal macrophages contacted with Caco-2 cell monolayer-permeable components of CV partially purified extracts or LPS.

Murine Macrophages Contacted with Caco-2 Cell-permeable Components of CV Partially Purified Extract In Vitro FIG. 22 illustrates the in vitro effect on the secretion of nitric oxide by murine peritoneal macrophages contacted with Caco-2 cell-permeable components of CV partially purified extract or LPS. The cell-permeable components of all CV partially purified samples were immunologically active, and all the samples had a greater activity than that of LPS. The lower molecular weight fractions and medium molecular weight fractions, C1D5E8 and C1D5E7, respectively, showed stronger activity than the higher molecular weight fraction, C1D5EX. The peptide-linked glucans in C1D5E8 and C1D5E7 have an average molecular weight of less than about 3 kDa.

Example XIX

Administration of CV Partially Purified Extract to Normal Mice

Study Design

Twenty-five ICR mice were sorted into five groups of 5 mice each. As shown in Table VIII the groups were treated as follows. Group 1 was treated with a C1D5E8, a CV partially purified extract administered i.p; Group 2 was treated with a C1D5E7, a CV partially purified extract administered i.p; Group 3 was treated with a C1D5E4, a CV partially purified extract administered i.p; Group 4 was treated with a C1D5EX, a CV partially purified extract administered i.p; and, Group 5 was treated with normal saline administered i.p., as a negative control.

Table VIII shows the dose and dosing schedule of each group. The mice of Groups 1–5 were sacrificed on day 8.

The CV crude extract was prepared and stored for i.p. or oral administration as described in Example VI, above.

TABLE VIII

| Treatment Group | Number of Mice | Cyclophosphamide Dose & Dosing Schedule | CV Dose & Dosing Schedule | Route of Administration |
|---|---|---|---|---|
| 1 | 5 | 20 mg/kg/day on day 1 (0.5 ml of 1 mg/ml solution injected into an approximately 25 g mouse) | C1D5E8 50 mg/kg/day on days 5–7 (0.25 ml of 5 mg/ml solution injected into an approximately 25 g mouse) | i.p. |
| 2 | 5 | 20 mg/kg/day on day 1 (0.5 ml of 1 mg/ml solution injected into an approximately 25 g mouse) | C1D5E7 50 mg/kg/day on days 5–7 (0.25 ml of 5 mg/ml solution injected into an approximately 25 g mouse) | i.p. |
| 3 | 5 | 20 mg/kg/day on day 1 (0.5 ml of 1 mg/ml solution injected into an approximately 25 g mouse) | C1D5E4 50 mg/kg/day on days 5–7 (0.25 ml of 5 mg/ml solution injected into an approximately 25 g mouse) | i.p. |
| 4 | 5 | 20 mg/kg/day on day 1 (0.5 ml of 1 mg/ml solution injected into an approximately 25 g mouse) | C1D5EX 50 mg/kg/day on days 5–7 (0.25 ml of 5 mg/ml solution injected into an approximately 25 g mouse) | i.p. |
| 5 | 5 | 20 mg/kg/day on day 1 (0.5 ml of 1 mg/ml solution injected into an approximately 25 g mouse) | 0.25 ml sterile normal saline pH 7.4 on days 5–7 | i.p. |

Figure 23A:
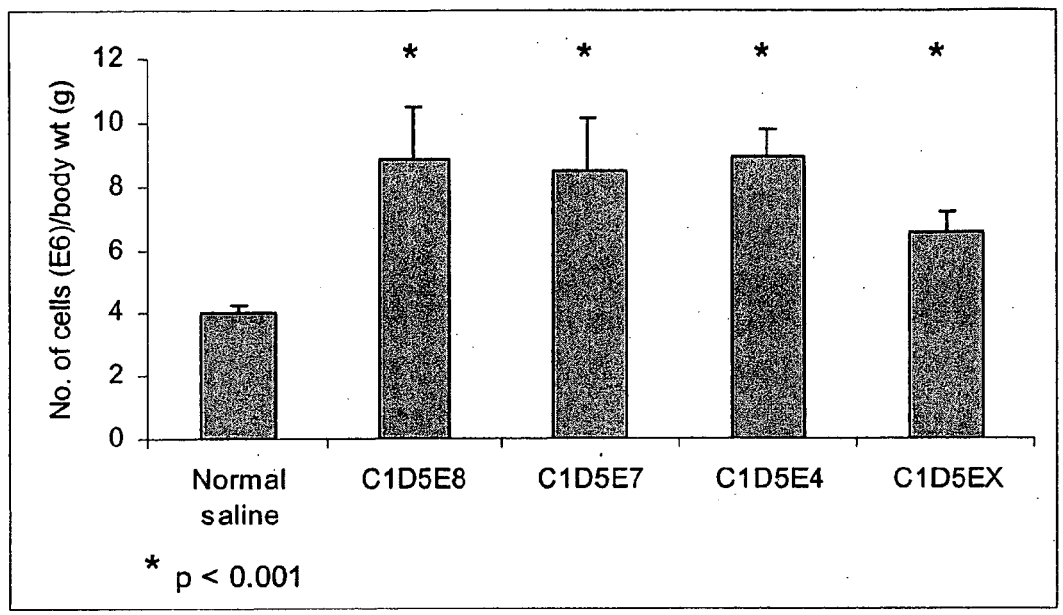
FIGS. 23A and 23B.

1. Effect of i.p. Administration of CV Partially Purified Extract on the In Vivo Proliferation of Viable Murine Splenocytes from Normal Mice All groups (Groups 1–4) ($p<0.001$) showed an increased in the number of in vivo viable splenocytes when compared to control mice (Group 5). (See FIG. 23A.) Groups 1–3, C1D5E8, C1D5E7, and C1D5E4, respectively, exhibited an increase in the number of splenocytes by about 100%. Group 4, C1D5EX (the CV partially purified extract with the highest molecular weight), showed an increase in the number of splenocytes of about 64%.

Splenocytes were harvested and isolated as described in Example III, above. The resulting cell suspension was prepared, and the viability of the cell suspension was tested as described in Example III, above.

Figure 23B:
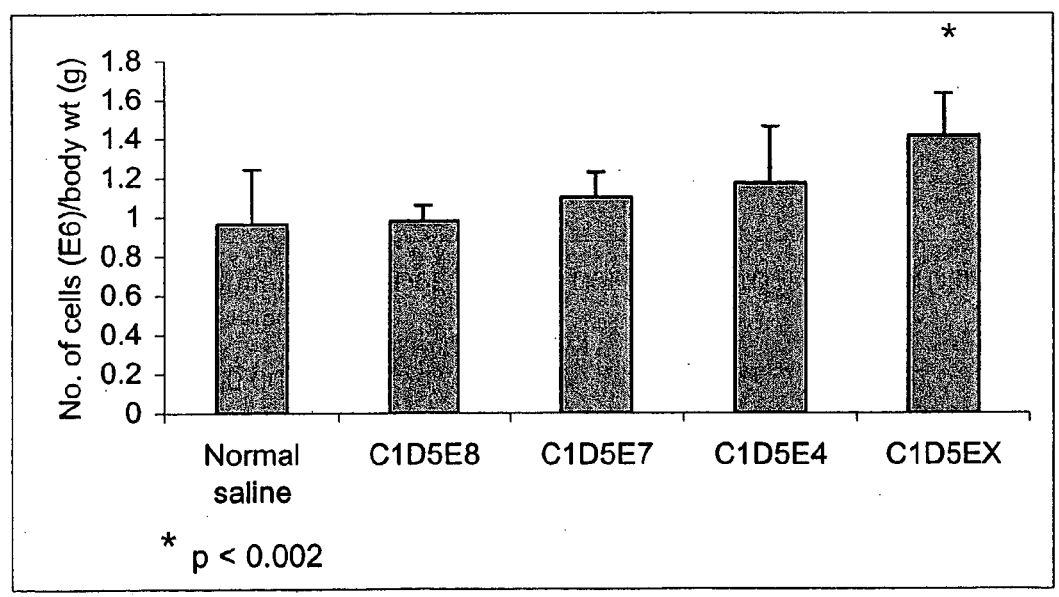

2. Effect of i.p. Administration of CV Partially Purified Extract on the In Vivo Proliferation of Viable Bone Marrow Cells from Normal Mice All groups (Groups 1–4) showed an increase in the number of in vivo viable bone marrow cell when compared to control mice (Group 5). (See FIG. 23B.) Only Group 4, C1D5EX, showed a statistically significant increase ($p<0.002$) in the number of viable bone marrow cells.

The bone marrow cells were harvested and isolated as described in Example IV, above. The resulting cell suspension was prepared, and the viability of the cell suspension was tested as described in Example III, above.

Example XX

Administration of CV Partially Purified Extract to Immunocompromised Mice

General Materials & Methods

Twenty-five ICR mice were sorted into five groups of 5 mice each. As shown in Table IX the groups were treated as follows. The mice of Groups 1–5 were immunosuppressed as described in Example VII, above. Group 1 was treated with a C1D5E8, a CV partially purified extract administered orally; Group 2 was treated with a C1D5E7, a CV partially purified extract administered orally; Group 3 was treated with a C1D5E4, a CV partially purified extract administered orally; Group 4 was treated with a C1D5EX, a CV partially purified extract administered orally; and, Group 5 was treated with deionized water administered orally, as a negative control. Table IX shows the dose and dosing schedule of each group. The mice of Groups 1–5 were sacrificed on day 8.

The cyclophosphamide was prepared and administered as described in Example VII, above. The CV crude extract was prepared and stored for i.p. or oral administration as described in Example VI, above.

TABLE IX

| Treatment Group | Number of Mice | CV partially purified fragment & Dose | CV Dosing Schedule | Route of Administration |
|---|---|---|---|---|
| 1 | 5 | C1D5E8 50 mg/kg/day (0.25 ml of 5 mg/ml solution orally into an approximately 25 g mouse) | On days 1–7 | oral |
| 2 | 5 | C1D5E7 50 mg/kg/day (0.25 ml of 5 mg/ml solution orally into an approximately 25 g mouse) | On days 1–7 | oral |
| 3 | 5 | C1D5E4 50 mg/kg/day (0.25 ml of 5 mg/ml solution orally into an approximately 25 g mouse) | On days 1–7 | oral |
| 4 | 5 | C1D5EX 50 mg/kg/day (0.25 ml of 5 mg/ml solution orally into an approximately 25 g mouse) | On days 1–7 | oral |
| 5 | 5 | 0.25 ml deionized water | On days 1–7 | oral |

Figure 24A:
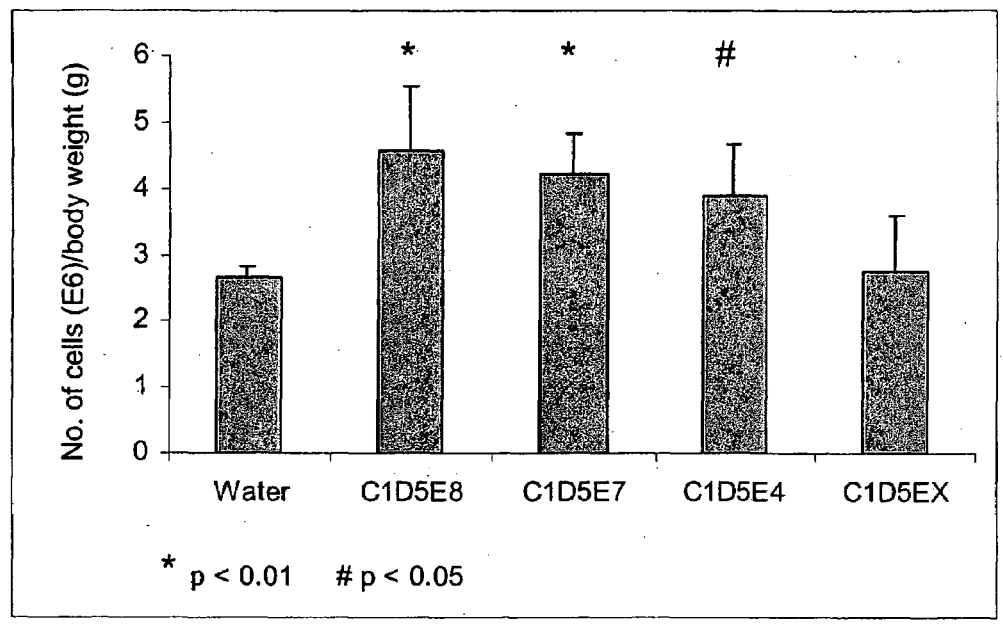
FIGS. 24A and 24B.

1. Effect of Oral Administration of CV Partially Purified Extract on the In Vivo Proliferation of Viable Murine Splenocytes from Immunocompromised Mice CV partially purified extract administered orally to the mice of Groups 1–4 increased the number of in vivo viable splenocytes when compared to control mice (Group 5). (See FIG. 24A.) C1D5E8 administered to Group 1 significantly increased (p<0.01) the number of in vivo viable splenocytes (by 66%) when compared to control mice (Group 5). C1D5E7 administered to Group 2 significantly increased (p<0.01) the number of in vivo viable splenocytes when compared to control mice (Group 5). C1D5E4 administered to Group 3 significantly increased (p<0.05) the number of in vivo viable splenocytes when compared to control mice (Group 5). C1D5EX administered to Group 4 did not increase the number of in vivo viable splenocytes significantly when compared to control mice (Group 5).

Splenocytes were harvested and isolated as described in Example III, above. The resulting cell suspension was prepared, and the viability of the cell suspension was tested as described in Example III, above.

Figure 24B:
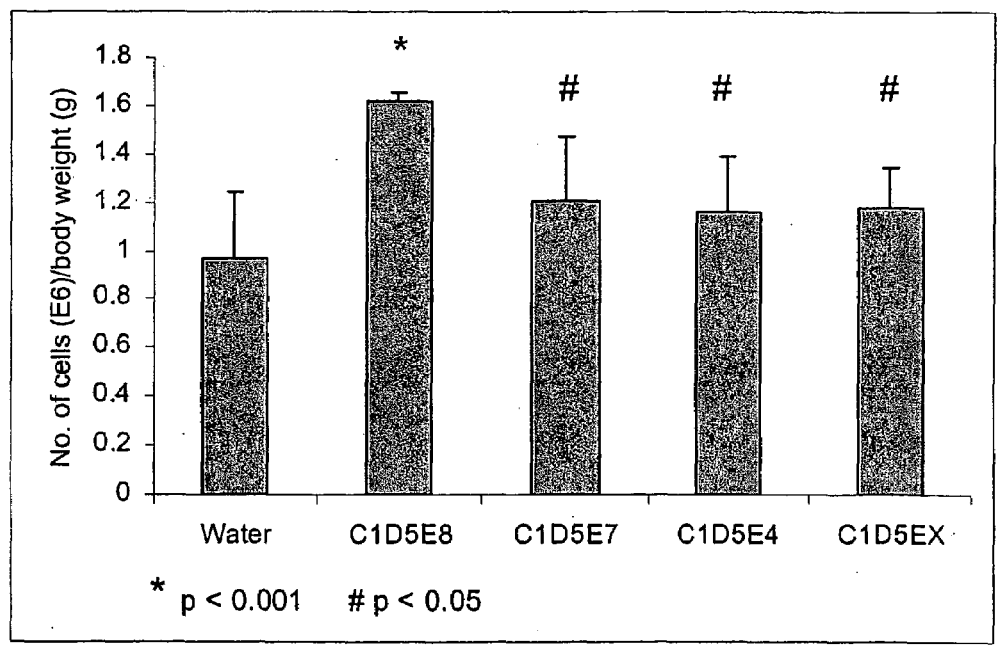

2. Effect of Oral Administration of CV Partially Purified Extract on the In Vivo Proliferation of Viable Bone Marrow Cells from Immunocompromised Mice All groups (Groups 1–4) showed an increased in the number of in vivo viable bone marrow cell when compared to control mice (Group 5). (See FIG. 24B.)

C1D5E8 administered to Group 1 significantly increased (p<0.001) the number of in vivo viable bone marrow cells when compared to control mice (Group 5). C1D5E7, C1D5E4, C1D5EX administered to Group 2, Group 3, and Group 4, respectively, significantly increased (p<0.05) the number of in vivo viable bone marrow cells when compared to control mice (Group 5).

The bone marrow cells were harvested and isolated as described in Example IV, above. The resulting cell suspension was prepared, and the viability of the cell suspension was tested as described in Example III, above.

1. Species Maintenance

Institute of Cancer Research (ICR) mice (in-bred strain) were supplied by the Animal House, The Chinese University of Hong Kong. The mice are housed no more than 20 animals per cage. The mice are housed in a facility where the temperature is maintained at 18–26° C., and the relative humidity is maintained between about 40–70%. The light/dark cycle is maintained on 12-hour intervals. The mice were maintained on a diet standard rodent chow. The mice used in the above examples weighed between 25–30 g, and were between 8–12 weeks old.

2. Caco Cell Culture

Caco-2 cells (purchased from American Type Culture Collection, Rockville, Md.) (passage 30 to 50) were grown and routinely maintained at 37° C. in DMEM medium supplemented with 25 mM D-glucose containing 10% FBS, 1% non-essential amino acids, 1% L-glutamine, 1 mM sodium pyruvate, penicillin (100 U/ml) and streptomycin (100 µg/ml) in an atmosphere of 5% $CO_2$ and 90% $O_2$ (all from Gibbs BRL, Life Technologies, Inc., Gaithersburg, Md.). The cells were harvested at about 70% confluence with 0.05% trypsin-EDTA and seeded on a polycarbonate filter, which was previously coated with type I collagen, (3.0 µm pores, 4.71 $cm^2$ growth area) inside the Transwell cell culture chambers (purchased from Costar-Coming, Rockville, Md.) at a cell density of $3 \times 10^5$ cells per filter. The culture medium (1.5 ml in the Transwell insert and 2.6 ml in the cluster plate) was replaced every 48 hrs. The monolayers were used on 21 to 25 days post seeding.

3. Buffers
Lysis Buffer
8.29 g $NH_4Cl$
1.002 g $NaHCO_3$
29.2 mg EDTA

All dissolved in 1 L deionized water, pH adjusted to 7.2, and sterilized by filtration through 0.22 µm sterile filters.

4. Complete Cell Culture Medium

RMPI 1640 medium (Gibco) incorporated with 10% v/v fetal bovine saline (FBS), 100 IU/ml penicillin, and 100 µg/ml streptomycin.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims. Unless otherwise apparent from the context, the elements, steps, features and embodiments of the invention described in this application can be used in all combinations with each other.

REFERENCES

1. Parslow T. G. The immune response. In *Medical Immunology*; Stites D. P., Terr A. I., Parslow T. G., Eds., Appleton and Lange: London, 1997; pp 63–73.
2. Tsukagoshi S. Krestin (PSK). *Cancer treatment review* 1984, 11, pp 131–155.
3. Descotes J. Assays of cell-mediated immunity. *An Introduction to Immunotoxicity*; Taylor & Francis Ltd: London, 1999; pp 103–110.
4. Descotes J. Strategies for the evaluation of immunosuppression. *An Introduction to Immunotoxicity*; Taylor & Francis Ltd: London, 1999; pp 125–136.
5. Lennernas H. Human intestinal permeability. *J. Pharm. Sci.*, 1998, 87(4), pp 403–410.
6. Borchardt R. T., Hidalgo I. J., Hillgren K. M., Hu M. Pharmaceutical applications of cell culture: an overview. In *Pharmaceutical Applications of Cell and Tissue Culture to Drug Transport*; Wilson G., Ed.; Plenum press: New York, 1991; pp 1–14.
7. Lee V. H. L. Peptide and protein drug delivery. In *Trends and Future Perspectives in Peptide and Protein Drug Delivery*; Lee V. H. L., Hashida M., Mizushima Y., Eds.; Harwood academic publishers: London, 1995; pp 3–15.
8. Ueno S., Yoshikumi C., Omura Y., Fujii T., Wada T., Takahashi E., Hirose F. U.S. Pat. No. 4,699,787: Nitrogen-containing polysaccharide, Oct. 13, 1987.
9. Ueno S., Yoshikumi C., Omura Y., Fujii T., Wada T., Takahashi E., Hirose F. U.S. Pat. No. 4,851,395: Nitrogen-containing polysaccharide, Jul. 25, 1989.
10. Ikuzawa M., Oguchi Y., Matsunaga K., Toyoda N., Furusho T., Fujii T., Yoshikumi C. U.S. Pat. No. 4,820,689: Pharmaceutical composition containing a glycoprotein, Apr. 11, 1989.
11. Ikuzawa M., Oguchi Y., Matsunaga K., Toyoda N., Furusho T., Fujii T., Yoshikumi C. U.S. Pat. No. 5,008,243: Pharmaceutical composition containing a glycoprotein, Apr. 6, 1991.
12. Suguira M., Ohno H., Sasaki Y., Hama K. U.S. Pat. No. 4,225,673: Glucan having antitumor activity, Sep. 30, 1980.
13. Yang M. P., Chen G. U.S. Pat. No. 5,824,648: Rnase-CV (*Coriolus versicolor*), Oct. 20, 1998.
14. Yang M. P., Chen G. U.S. Pat. No. 6,087,335: Rnase-CV (*Coriolus versicolor*), Jul. 11, 2000.

What is claimed is:

1. A purified extract of *Coriolus versicolor* comprising at least one peptide-linked glucan wherein all of the at least one peptide linked glucans consist of glucose molecules linked by a (1→3) linkage, having a molecular weight of 0.3 kDa to 5 kDa as determined by size exclusion chromatography; and having immune stimulating activity.

2. The purified extract of claim 1, wherein the molecular weight is 0.7 kDa.

3. The purified extract of claim 1, wherein the average molecular weight is 2.6 kDa.

4. The purified extract of claim 2, wherein the peptide-linked glucan is capable of intestinal absorption as determined by the Caco-2 cell monolayer Transwell method.

5. The purified extract of claim 3, wherein the peptide-linked glucan is capable of intestinal absorption as determined by the Caco-2 cell monolayer Transwell method.

6. The purified extract of claim 1, prepared by
treating *Coriolus versicolor* with alkali, and separating a supernatant;
subjecting the supernatant to cationic exchange;
subjecting eluate from the cationic exchange to anionic exchange;
subjecting eluate from the anionic exchange to a size fractionation technique, and collecting a fraction comprising the at least one peptide-linked glucan.

7. The purified extract of claim 6, wherein the size fractionation technique is molecular exclusion chromatography or ethanolic fractionation.

8. The purified extract of claim 6, wherein the cationic exchange is performed on a CM cellulose column.

9. The purified extract of claim 6, wherein the anionic exchange is performed on a DEAE cellulose column.

10. The purified extract of claim 1, wherein the peptide-linked glucan is soluble in water, ethanol, and acetone, is insoluble in chloroform and dichloroform, and is non-hygroscopic.

* * * * *